(12) United States Patent
Wagner et al.

(10) Patent No.: US 9,340,650 B2
(45) Date of Patent: May 17, 2016

(54) HYDROPHILIC/LIPOPHILIC MODIFIED POLYSILOXANES AS EMSULSIFIERS

(75) Inventors: Roland Wagner, Bonn (DE); Walter Simon, Leverkusen (DE); Martin Kropfgans, Rheinmünster (DE); Sabine Nienstedt, Hannover (DE); Albert Schnering, Leverkusen (DE); Katharina Streicher, Leverkusen (DE); Karl-Heinz Sockel, Leverkusen (DE); Sebastian Maass, Elsdorf (DE)

(73) Assignee: Momentive Performance Materials GmbH, Leverkusen (DE)

( * ) Notice: Subject to any disclaimer, the term of this patent is extended or adjusted under 35 U.S.C. 154(b) by 0 days.

(21) Appl. No.: 13/511,464

(22) PCT Filed: Nov. 24, 2010

(86) PCT No.: PCT/EP2010/068131
§ 371 (c)(1),
(2), (4) Date: Jul. 12, 2012

(87) PCT Pub. No.: WO2011/064255
PCT Pub. Date: Jun. 3, 2011

(65) Prior Publication Data
US 2012/0289649 A1  Nov. 15, 2012

(30) Foreign Application Priority Data

Nov. 24, 2009  (DE) .................. 10 2009 047 077
Apr. 26, 2010  (EP) ..................................... 10161056

(51) Int. Cl.
| | |
|---|---|
| *C08G 77/14* | (2006.01) |
| *C08G 77/388* | (2006.01) |
| *A61K 8/893* | (2006.01) |
| *A61K 8/895* | (2006.01) |
| *A61K 8/898* | (2006.01) |
| *A61Q 19/00* | (2006.01) |
| *B01D 19/04* | (2006.01) |
| *C08G 77/46* | (2006.01) |
| *C08L 83/08* | (2006.01) |
| *C08L 83/12* | (2006.01) |

(52) U.S. Cl.
CPC .............. *C08G 77/388* (2013.01); *A61K 8/893* (2013.01); *A61K 8/895* (2013.01); *A61K 8/898* (2013.01); *A61Q 19/00* (2013.01); *B01D 19/0409* (2013.01); *C08G 77/14* (2013.01); *C08G 77/46* (2013.01); *C08L 83/08* (2013.01); *C08L 83/12* (2013.01)

(58) Field of Classification Search
CPC ....... C08G 77/12; C08G 77/388; C08G 77/14
USPC .......................................................... 528/26
See application file for complete search history.

(56) References Cited

U.S. PATENT DOCUMENTS

| | | | |
|---|---|---|---|
| 3,389,160 A | 6/1968 | Reid | |
| 4,978,726 A * | 12/1990 | Dohler et al. | .................. 525/479 |
| 7,635,581 B2 | 12/2009 | Ferenz et al. | |
| 7,855,265 B2 | 12/2010 | Thum et al. | |
| 2007/0184006 A1 * | 8/2007 | Ferenz et al. | ............. 424/70.12 |
| 2009/0062459 A1 | 3/2009 | Thum et al. | |
| 2013/0121946 A1 * | 5/2013 | Randall et al. | ............. 424/70.17 |

FOREIGN PATENT DOCUMENTS

| | | |
|---|---|---|
| EP | 0535596 A1 | 4/1993 |
| EP | 0879840 B2 | 11/1998 |
| WO | 2006/127883 A2 | 11/2006 |

OTHER PUBLICATIONS

Lundblad (Biochemistry and Molecular Biology Compendium, CRC Press, (2007), p. 327).*
International Search Report for corresponding PCT/EP2010/068131 mailed Mar. 3, 2011, three pages.
International Preliminary Report on Patentability for corresponding PCT/EP2010/068131 issued May 30, 2012, eight pages.
Espacenet bibliographic data for JPS6268820 published Mar. 28, 2987, one page.
Espacenet bibliographic data for JPS63139106 published Jun. 10, 1988, two pages.
Espacenet bibliographic data and partial translation for DE19524815 published Jan. 9, 1997, three pages.

* cited by examiner

*Primary Examiner* — Kuo-Liang Peng
(74) *Attorney, Agent, or Firm* — Rankin, Hill & Clark LLP

(57) ABSTRACT

The invention concerns polysiloxane compounds as W/O-emulsifiers, in textile softeners, antifoams, foam stabilizers and agriculture chemicals, in particular as W/O-emulsifiers for cosmetic uses.

13 Claims, No Drawings

HYDROPHILIC/LIPOPHILIC MODIFIED POLYSILOXANES AS EMSULSIFIERS

The invention concerns hydrophilic and lipophilic modified polysiloxanes which preferably comprise ester units and which are preferably suitable as emulsifiers, in textile softeners, antifoams, foam stabilizers, demulsifiers and agriculture chemicals, in particular as W/O-emulsifiers for cosmetic uses.

Siloxane based W/O-emulsifiers comprising ethylene oxide units are used extensively in liquid to paste-like cosmetic formulations such as, e.g. creams and lotions (US 2005/0008592, US 2004/0009131). By using these emulsifiers it has become possible to emulsify large amounts of water in oil (high internal phase ratio emulsions). Such emulsions effect a pleasant, light feeling on the skin.

Furthermore, the use of such emulsifiers in solid formulations has been described (U.S. Pat. No. 7,199,095, U.S. Pat. No. 7,083,800).

In this context it has been shown that oils differing strongly with regard to the molecular weight and the polarity, such as e.g. hydrocarbons, fatty acid esters and silicone oils can be emulsified so as to be stable long-term. This is due to the chemical structure of such siloxane based W/O-emulsifiers, which are made up of a siloxane backbone chain, hydrophilic polyethylene oxide units and hydrophobic long chain alkyl groups. The hydrophilic polyether units mediate the connection to the water phase, the long chain alkyl groups bond the oil phase and the siloxane backbone chain stays in the phase boundary (U.S. Pat. No. 4,698,178; D. Schäfer, Tenside Surf. Det. 1990, 3, 154; B. Grüning, P. Hameyer, C. Weitemeyer, Tenside Surf. Det. 1992, 2, 78).

During the further development of this approach it was suggested to create emulsifiers by cohydrosilylation of SiH-containing siloxanes with allyl polyethers and undecenoic acid fatty alcohol esters (U.S. Pat. No. 6,388,042) or undecenoic acid fluoroalcohol esters (U.S. Pat. No. 6,727,340) respectively, which have good compatible and degradable fatty acid units as oil compatible components.

As an alternative, trials were undertaken to convert polyethylene oxide based siloxanes by esterification with fatty acids or esterification with dicarboxylic acids respectively in combination with alkoxylated fatty acids, alkoxylated fatty alcohols, glycerine fatty acids or neutralization of the carbon acid function with fatty amines into W/O-emulsifiers (U.S. Pat. No. 5,226,923, U.S. Pat. No. 5,180,843, U.S. Pat. No. 5,136,063, U.S. Pat. No. 6,891,051, U.S. Pat. No. 5,475,125, U.S. Pat. No. 5,446,184, U.S. Pat. No. 5,446,183, U.S. Pat. No. 5,411,729, U.S. Pat. No. 5,248,783, U.S. Pat. No. 5,210,133). A specific disadvantage of this product group is that hydrophilic and hydrophobic groups cannot orientate independently of one another.

A general disadvantage of all of these ethylene oxide units containing, siloxane based W/O-emulsifiers is that the proportion of polyethylene oxide units contained therein in combination with sunlight is made responsible for skin sensitisations.

It is further well known to use glycerine modified siloxanes as a spreading additive (US 2005/0261133). Polyglycerole modified siloxanes have become known as a component in formulations for the treatment of fibres (JP 2005-082925). Branched polyglycerole modified siloxanes are discussed in US 2005/0084467 and JP 2005-089494. Further modified siloxanes are described in EP 2030605, EP 2243799, EP 1816154 and references cited therein.

For the prevention of the skin sensitization problems discussed above, siloxane-based W/O-emulsifiers have been presented, which are based on the cohydrosilylation of SiH-containing siloxanes with unsaturated oligoglycerines and long-chained alkenes (SÖFW-Journal, 132, 12-2006, 31).

The etherification of the polyglycerine units positioned on the siloxane chain with e.g. lauryl alcohol results in emulsifiers, which are to be used in solid W/O-emulsions (US 2006/0013793). Again, this solution is disadvantageous in that hydrophilic and hydrophobic groups cannot orientate independently of one another. Dibenhates derived from allyl glycerol were added to α,ω-SiH siloxanes and resulted in waxes, which do not comprise emulsifying characteristics (US 2003/0096919). This is also the case for those waxes, which are derived from allyl alcohol fatty acid esters (US 2004/0071741).

None of the afore-mentioned solutions describes a way to ethylene oxide-free siloxane-based W/O-emulsifiers which have readily degradable hydrophobic fatty acid ester units and at the same time comprise hydrophilic hydroxylated carboxylic acid ester units, wherein these hydrophobic fatty acid units can be introduced independently from the hydrophilic hydroxylated carboxylic acid ester units. Thus, it is the object of the invention to describe the synthesis of polyethylene oxide-free siloxane-based W/O-emulsifiers which have readily degradable fatty acid units as an oil soluble component and at the same time comprise hydroxylated carboxylic acid ester units as a hydrophilic component and wherein the addition of the hydrophilic and hydrophobic components can follow independently of one another. It is a further object of the invention to describe the use of the polyethylene oxide-free siloxane-based W/O-emulsifiers in cosmetic formulations.

It was surprisingly found that polysiloxane compositions of the formula:

$$[M_a D_b T_c Q_d]_e \qquad (I)$$

wherein
$M = R_3SiO_{1/2}$,
$D = R_2SiO_{2/2}$,
$T = RSiO_{3/2}$,
$Q = SiO_{4/2}$,
with
a=1-10
b=0-1000
c=0-1
d=0-1
e=1-10
wherein
R=is an organic group,
with the requirement that R comprises at least one group, preferably at least two groups $R^9$ which are selected from:
$R^1 = $—Z-(A-E)$_y$, wherein
Z=a bivalent or trivalent straight-chained, cyclic or branched, saturated or unsaturated $C_2$ to $C_{20}$ hydrocarbon residue which can comprise one or more groups selected from —O—, —NH—,

and can be substituted by one or more OH groups,
A is a bivalent residue which is selected from the group which consists of:

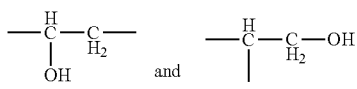

y=1 or 2

E is selected from the group which consists of:

$E^2$=—O—C(O)—$R^2$, wherein $R^2$=is a straight-chained, cyclic or branched, saturated or unsaturated hydrocarbon residue with up to 50 hydrocarbon atoms, which can comprise one or more groups selected from —O—, —NH—, —$NR^3$—, —C(O)—, and is substituted by one or more OH groups, wherein $R^3$=a straight-chained, cyclic or branched, saturated or unsaturated hydrocarbon residue with up to 6 hydrocarbon atoms, and $E^3$=

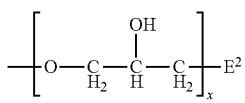

wherein $E^2$ is as defined above, and x=1-4, $E^5$=—$NR^4R^5$, wherein $R^4$ and $R^5$ are the same or different and are selected from the group which comprises: hydrogen and a straight-chained, cyclic or branched, saturated or unsaturated hydrocarbon residue with up to 30 carbon atoms, which can comprise one or more groups selected from —O—, —NH—, —$NR^3$—, wherein $R^3$, is as defined above, —C(O)—, and can be substituted by one or more OH— and/or $H_2N$ groups, and $R^6$=—Z-$E^2$ wherein $E^2$ is defined as above, and $R^7$=—Z-$E^6$, wherein $E^6$=—NH—C(O)—$R^4$, wherein $R^4$ is defined as above, and $R^9$—in addition to at least one of $R^1$, $R^6$ and $R^7$—may be $R^{61}$=—Z-$E^1$, wherein $E^1$ is —O—C(O)—$R^{21}$, wherein $R^{21}$=a straight-chained, cyclic or branched, saturated or unsaturated hydrocarbon residue with up to 50 carbon atoms, which can comprise one or more groups selected from —O—, —NH—, —$NR^3$—, —C(O)—, wherein $R^3$ is as defined above, but has no hydroxy substituent, could solve the problems defined above, particularly of the preparation of the emulsifiers, which substantially do not comprise polyalkylene oxide groups, and are able to emulsify with a high stability extremely high amounts of water in a broad spectrum of various water-insoluble phases.

Accordingly, the polysiloxane compounds according to the invention substantially do not comprise polyalkylene oxide units, such as, in particular, polyethylene oxide and/or polypropylene oxide units with more than 4 repetitive units of alkylene oxides. Preferably the polysiloxane compounds according to the invention do not comprise polyalkylene oxide units.

In a preferred embodiment the polysiloxane compounds according to the invention comprise siloxy structural elements selected from the following formulas:

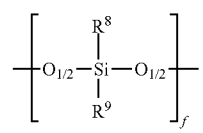

wherein $R^8$=$C_1$ to $C_{22}$-alkyl, fluoroalkyl or aryl, and $R^9$=$R^1$, $R^6$ and/or $R^7$, and optionally $R^{61}$, f=0-600,

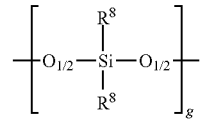

wherein the groups $R^8$ can be the same or different and are selected from $C_1$ to $C_{22}$-alkyl, fluoro-substituted $C_1$ to $C_{22}$-alkyl and aryl, and g=0-700,

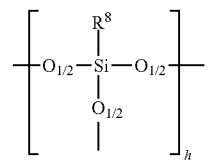

wherein $R^8$ is as defined above, and h=0-10,

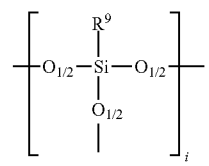

wherein $R^9$ is as defined above, and i=0-10,

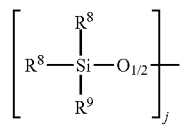

wherein $R^8$ and $R^9$ are as defined above, and j=0-30,

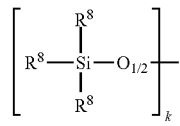

wherein $R^8$ and $R^9$ are as defined above, and k=0-30,

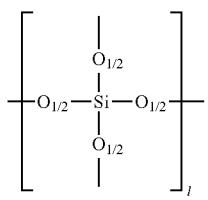

wherein l=0-10, f+g+h+i+j+k+l=12 to 1000.

In a particularly preferred embodiment the polysiloxane compounds according to the invention comprise two or more different residues $R^9=R^1$, $R^6$ and/or $R^7$ and optionally $R^{61}$. Preferably, the residues $R^9$ are selected from the residues $R^1$ and $R^6$.

In a further preferred embodiment of the polysiloxane compounds according to the invention, the residues $R^9=R^1$, $R^6$ and/or $R^7$, preferably the residues $R^1$ and/or $R^6$, comprise one or more, preferably one (1), ester units (—C(O)O—).

In further preferred embodiments $R^9$ is selected according to the following clauses:

$R^9$ is $R^1$ and/or $R^6$, and optionally $R^{61}$, or $R^9$ is $R^7$, and optionally $R^{61}$, or $R^9$ is $R^1$ and/or $R^6$ and $R^7$, and optionally $R^{61}$, the latter embodiment according to which $R^9$ comprises a hydroxy carboxylic acid residue $R^1$ and/or $R^6$ and an amino-functional residue $R^7$ being particularly preferred.

In a further preferred embodiment the polysiloxane compounds according to the invention comprise two or more different residues $R^9$, which differ in their hydrophilic/lipophilic characteristics, corresponding to the hydrophilic residues $R^{91}$ and the lipophilic residues $R^{92}$.

In a further preferred embodiment the polysiloxane compounds according to the invention comprise the hydrophilic residues $R^{91}$, which have a log P (25° C.) of <0.5, and the lipophilic residues $R^{92}$, which have a log P (25° C.) of ≥0.5, wherein log P (25° C.) corresponds to the distribution coefficient of the corresponding compounds H—$R^{91}$ and H—$R^{92}$, corresponding to the compounds H—$R^1$, H—$R^6$ (and H—$R^{61}$ according to the optionally present residue $R^{61}$) and H—$R^7$ in a water-n-octanol mixture at 25° C. According to the invention the corresponding distribution coefficients are determined for the sake of simplicity by means of the commercially available log P calculating software by the company ACD (ACD Inc., 133 Richmond St. W., Suite 605, Toronto, ON, Canada M5H 2L3 e.g. in Perspectives in Drug Discovery and Design, 19: 99-116, 2000), which are based on well-characterized log P contributions of single atoms structure fragments and intramolecular interaction between different fragments. Alternatively, the experimental determination in a water/n-octanol mixture (water: 50 ml, octanol: 50 ml, substance to be determined H—$R^{91}$ and H—$R^{92}$: 1 ml) at 25° C. is also possible.

In a further preferred embodiment the polysiloxane compounds according to the invention comprise structural elements selected from the following formulas:

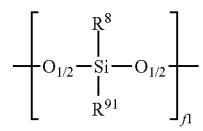

wherein $R^8=C_1$ to $C_{22}$-alkyl, fluoroalkyl or aryl, preferably methyl, $R^{91}$ is as defined above or below, and f1=1-300, preferably 2 to 200, more preferably 2 to 50, even 3 to 30,

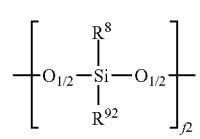

wherein $R^8=C_1$ to $C_{22}$-alkyl, fluoroalkyl or aryl, preferably methyl, and $R^{92}$ is as defined above or below, and f2=1-300, preferably 2 to 200, more preferably 2 to 50, even 4 to 40,

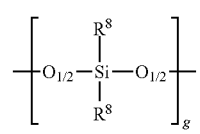

wherein the groups $R^8$ can be the same or different and are selected from $C_1$ to $C_{22}$-alkyl, fluoro-substituted $C_1$ to $C_{22}$-alkyl and aryl, preferably methyl, and g=0-700, preferably 3 to 500, more preferably 5 to 200, even more preferably 10 to 100,

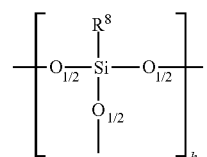

wherein $R^8$ is, as defined above, preferably methyl, and h=0-10, preferably 0,

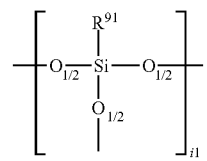

wherein $R^{91}$ is as defined above or below, and i1=0-5, preferably 0,

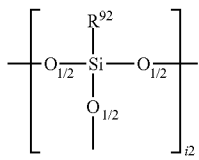

wherein $R^{92}$ is as defined above or below, and
i2=0-5, preferably 0,

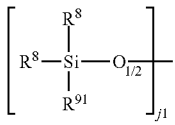

wherein $R^8$ is, as defined above, preferably methyl, and $R^{91}$ is as defined above or below, and
j1=0-15, preferably 0,

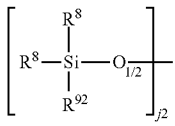

wherein $R^8$ is, as defined above, preferably methyl, and $R^{92}$ is as defined above or below, and
j2=0-15, preferably 0,

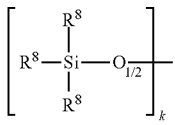

wherein $R^8$ is, as defined above, preferably methyl, and
k=0-30, preferably 1 to 6, more preferably 2,

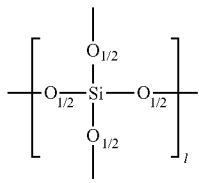

wherein l=0-10, preferably 0,
f1+f2+g+h+i1+i2+j1+j2+k+l=12 to 1000, preferably 15 to 400, more preferably 20 to 200, even more preferably 30 to 150.

Preferably the molar ratio of the hydrophilic residues $R^{91}$ and the lipophilic residues $R^{92}$ in the polysiloxane compounds according to the invention amounts to from 5:1 to 1:10, more preferably from 2:1 to 1:7, even more preferably from 1:1 to 1:5.

In a preferred embodiment the group $R^{91}$ and the lipophilic residues $R^{92}$ in the polysiloxane compounds according to the invention amounts to from 5:1 to 1:100, more preferably from 5:1 to 1:50.

Preferably the molar ratio of the $R^{91}$ as well as $R^{92}$-comprising siloxy units to the "non-modified", only $R^8$-comprising siloxy units is 5:1 to 1:10, more preferably 2:1 to 1:7, even more preferably from 1:1 to 1:5. The polysiloxane compounds in which the ratio $R^{91}$ to $R^{92}$ is equal to 1 and less than 1, are preferably used as W/O-emulsifiers, as foam stabilisers for polyurethane foams, demulsifiers in the oil and gas industry, or also as defoamers or in defoaming formulations for e.g. diesel fuels or as coating additive for flow and levelling of paints coating compositions, as additive for anti-blocking, mar resistance, as lubricant or lubricating additive, as tissue softeners or in tissue softener compositions as self-emulsifying alkylene oxide-free softener or as shear stable emulsifier in textile treatment formulations.

If the ratio $R^{91}$ to $R^{92}$ is the same or greater than 1, the use as defoamers, compatibilisators for lipophilic phases, e.g. O/W-emulsions and particularly preferred is the use as demulsifiers in the oil and gas industry for faster and better separation of crude oil and water, coagulant for rubber latex, as additive for anti-blocking, mar resistance, as lubricant or lubricating additive, as tissue softeners or in tissue softener composition as self-emulsifying alkylene oxide-free softener or as shear stable emulsifier in textile treatment formulations, as foam stabilizers for aqueous foams indetergents, dishwashing liquids and in general-purpose cleaners, cosmetic fatty phases such as creams, plastic and thermoplastic or elastomer additives for hydrophilisation and the improved wettability of thermoplastic or elastomeric surfaces.

It is particularly preferred that the polysiloxane compounds according to the invention comprise siloxy units of the formulas:

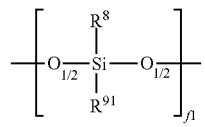

wherein $R^8=C_1$ to $C_{22}$-alkyl, fluoroalkyl or aryl, preferably methyl,
$R^{91}$ is as defined above or below, and
f1=1-300, preferably 2 to 200, more preferably 2 to 50, even 3 to 30,

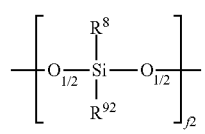

wherein $R^8=C_1$ to $C_{22}$-alkyl, fluoroalkyl or aryl, preferably methyl, and
$R^{92}$ is as defined above or below, and
f2=1-300, preferably 2 to 200, more preferably 2 to 50, even 4 to 40,

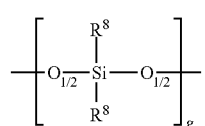

wherein $R^8=C_1$ to $C_{22}$-alkyl, fluoroalkyl or aryl, preferably methyl, and
g=0-700, and

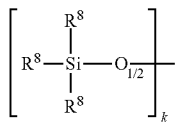

wherein the groups $R^8$ can be the same or different and can be selected from $C_1$ to $C_{22}$-alkyl, fluoro-substituted $C_1$ to $C_{22}$-alkyl and aryl, preferably methyl and k=2.

Accordingly, the polysiloxane compounds according to the invention preferably are linear trimethylsilyl end-stopped polysiloxane compounds.

In further preferred embodiments of the polysiloxane compounds according to the invention at least one, several or all of the following definitions are fulfilled in each case:

R selected from: $C_1$ to $C_{10}$-alkyl, which, if necessary, can be substituted with 1 to 13 fluoro atoms, and aryl, and $R^9$ is selected from $R^1$, $R^6$ and $R^7$, and optionally in addition $R^{61}$ may be presesent as $R^9$ Z=a bivalent or trivalent straight-chained, cyclic or branched, saturated or unsaturated $C_2$ to $C_{10}$-hydrocarbon residue, which can comprise —O— groups and can be substituted by one or more OH groups, g=10 to 700, preferably 10 to 200, preferably 10 to 150, preferably 20 to 150, preferably 30 to 150, preferably 30 to 100, f1=1 to 200, preferably 1 to 100, preferably 1 to 50, preferably 1 to 30, preferably 3 to 30, preferably 5 to 30, f2=1 to 200, preferably 1 to 100, preferably 1 to 50, preferably 1 to 30, preferably 3 to 30, preferably 5 to 30, h=0 to 5 and preferably 0,
i1=0 to 5 and preferably 0,
i2=0 to 5 and preferably 0,
l=0 to 5 and preferably 0,
f1+f2+g+h+i1+i2+j1+j2+k+l=10 to 500, preferably 10 to 200, preferably 10 to 150, preferably 20 to 150, preferably 30 to 150, preferably 30 to 100.

In further preferred embodiments of the polysiloxane compounds according to the invention one, several or all of the following definitions are fulfilled in each case:

R is selected from: $C_1$ to $C_6$-alkyl, which, if necessary, can be substituted with 1 to 13 fluoro atoms, phenyl, Z=a bivalent or trivalent straight-chained, cyclic or branched, saturated or unsaturated $C_2$ to $C_6$-hydrocarbon residue, which can comprise one or more —O— groups and can be substituted by one or more OH groups, y=1,
$R^2$=a straight chained, cyclic or branched, saturated or unsaturated hydrocarbon residue with up to 30 carbon atoms, which can comprise one or more groups selected from —O—, —NH—, —$NR^3$—, —C(O)— and can be substituted by one or more OH groups, wherein $R^3$ is as defined above.

Further preferred embodiments of the polysiloxane compounds according to the invention are characterized in that R in each case comprises at least one, preferably in each case several of the groups $R^{91}$ and $R^{92}$ (i.e. the groups $R^{91}$ as well as $R^{92}$ are present), wherein $R^{91}$ is selected from the group, which comprises:
$R^{11}$=—Z-(A-E)$_y$, wherein
E is selected from the group, which comprises:
$E^2$=—O—C(O)—$R^{22}$,
wherein $R^{22}$=a straight-chained, cyclic or branched, saturated or unsaturated hydrocarbon residue with up to 9 carbon atoms, which can comprise one or more groups selected from —O—, —NH—, —$NR^3$—, —C(O)—, and is substituted by one or more OH groups, wherein $R^3$=a straight-chained, cyclic or branched, saturated or unsaturated hydrocarbon residue with up to 6 carbon atoms, and $E^3$=

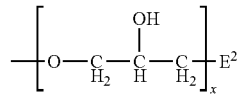

wherein $E^2$ is as defined before (i.e. $E^2$=—O—C(O)—$R^{22}$), and x=1-4,
$E^5$=—$NR^{41}R^{51}$, wherein
$R^{41}$ and $R^{51}$ are the same or different and selected from the group comprising: a hydrogen and straight-chained, cyclic or branched, saturated or unsaturated hydrocarbon residue with up to 9 carbon atoms, which can comprise one or more groups selected from —O—, —NH—, —$NR^3$—, wherein $R^3$, as defined above, can comprise —C(O)— and can be substituted by one or more OH and/or $H_2N$ groups, and
$R^6$=—Z-$E^2$ wherein $E^2$ is as defined before for $R^{11}$ (i.e. $E^2$=—O—C(O)—$R^{22}$),
$R^7$=—Z-$E^6$, wherein $E^6$=—NH—C(O)—$R^{22}$, wherein $R^{22}$ is defined above, and
$R^{92}$ is selected from the group, which comprises:
$R^1$=—Z-(A-E)$_y$, wherein
E is selected from the group, which comprises:
$E^2$=—O—C(O)—$R^{23}$,
wherein $R^{23}$=a straight-chained, cyclic or branched, saturated or unsaturated hydrocarbon residue with 10 to 50 carbon atoms, which can comprise one or more groups selected from —O—, —NH—, —$NR^3$—, —C(O)—, and can be substituted by one or more OH groups (which case includes long chain hydroxy fatty acid residues, like e.g. ricinoleic acid—a less preferred embodiment), wherein $R^3$=a straight-chained, cyclic or branched, saturated or unsaturated hydrocarbon residue with up to 6 carbon atoms, and $E^3$=

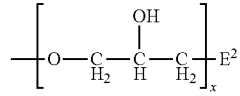

wherein $E^2$ is as defined before for $R^{92}$ (i.e. —O—C(O)—$R^{23}$), and x=1-4,
$E^5$=—$NR^{42}R^{52}$, wherein
$R^{42}$ and $R^{52}$ are the same or different and are selected from the group comprising: a hydrogen and straight-chained, cyclic or branched, saturated or unsaturated hydrocarbon residue with 10 to 30 carbon atoms, which can comprise one or more groups selected from —O—, —NH—, —$NR^3$—, wherein $R^3$ is as defined above, —C(O)—, and can be substituted by one or more OH— and/or $H_2N$ groups, and
$R^6$=—Z-$E^2$ wherein $E^2$ is as defined before for $R^{92}$,
$R^7$=—Z-$E^6$, wherein $E^6$=—NH—C(O)—$R^{42}$, wherein $R^{42}$ is as defined above.

In further preferred embodiments of the polysiloxane compounds according to the invention, at least one, several or all of the following definitions are fulfilled in each case:

R is selected from methyl, $R^{91}$ and $R^{92}$, wherein $R^{91}$ and $R^{92}$ is each defined as above,
$Z=$—$CH_2CH_2CH_2$—O—$CH_2$—, —$CH_2CH_2CH_2$—,

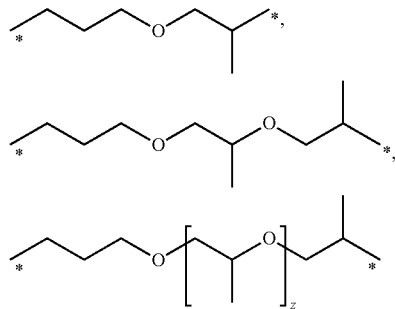

z=1 to 4,
(wherein * marks a bond in each case)
—CH=$CH_2CH_2$—, —CH=$CH_2CH_2CH_2$—,

wherein the bond to the silicon takes places in the 2-position.
x=1.
Particularly
$R^8=C_1$ to $C_6$-alkyl, fluoroalkyl or phenyl,
Z=bivalent straight-chained, cyclic or branched, saturated or unsaturated $C_1$ to $C_8$-hydrocarbon residue, which can comprise one or more —O—, —NH—,

—C(O)— groups, and can be substituted by one or more OH groups,
Especially preferred are
$R^8$=methyl,
—Z—=

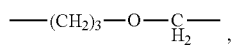

particularly in the $R^6$=—Z-$E^2$ version, Z can also be selected from the cyclic structures which are derived from cyclic epoxides, such as

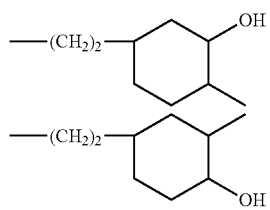

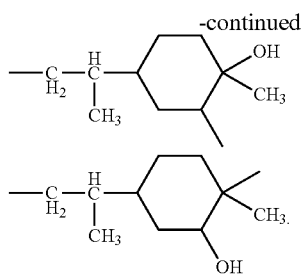

According to the invention, the polysiloxane compounds are preferably produced by the following processes, which are characterized in that
(a) an epoxy functional polysiloxane is reacted with one or more, preferably more carboxylic acids and, if necessary, subsequently with primary or secondary amines,
(b) an epoxy functional polysiloxane is reacted with one or more, preferably more carboxylic acids and carboxylic acid anhydrides, wherein the carboxylic acid anhydrides, if necessary, are partially esterified by the addition of monovalent or polyvalent alcohols, and, if necessary, also subsequently with primary or secondary amines,
(c) a SiH functional polysiloxane is reacted with
 (i) one or more mono-functional olefinic or acetylenic unsaturated ethers of glycerine or of glycerine oligomers whose hydroxyl groups, if necessary, can be silylated and/or acetalised and/or ketalised and/or esterified, and
 (ii) one or more esters of fatty acids with unsaturated alcohols,
(d) amino functional polysiloxanes are esterified with carboxylic acids or reacted with epoxy functional compounds.

More specifically the following synthetic pathways are available:
(a) a saturated or unsaturated epoxy functional polysiloxane is reacted with a mixture, containing short chained, preferably hydroxy functionalized, carboxylic acids and long chained, preferably hydroxy free, carboxylic acids, and optionally afterwards with primary or secondary amines,
(b) a saturated or unsaturated epoxy functional polysiloxane is reacted with a mixture, containing short chained, preferably hydroxy functionalized, carboxylic acids and long chained, preferably hydroxy free, carboxylic acids, and optionally afterwards with primary or secondary amines, wherein the carboxylic acids are obtained by partial esterification or amidation of carboxylic acid anhydrides with corresponding alcohols or amines,
(c) a saturated or unsaturated epoxy functional polysiloxane is reacted with long chained, preferably hydroxy free, carboxylic acids, and optionally afterwards with primary or secondary amines, wherein optionally the carboxylic acids can be obtained by partial esterification or amidation of carboxylic acid anhydrides with corresponding alcohols or amines,
(d) a SiH functionalized polysiloxane is reacted with
one or more than one monofunctional acetylenically unsaturated ether of glycerol or glycerol oligomers, optionally having silylated, acetylated, ketalized or esterified OH groups,
and
one or more than one ester of fatty acids with olefinically or acetylenically unsaturated alcohols (e) a SiH functionalized polysiloxane is reacted with
one or more than one monofunctional olefinically unsaturated ether of glycerol or glycerol oligomers, optionally having silylated, acetylated, ketalized or esterified OH groups,
and
one or more than one ester of fatty acids with acetylenically unsaturated alcohols
(f) a SiH functionalized polysiloxane is reacted with
one or more than one monofunctionally unsaturated alkyne or alkene and one or more than one monofunctional olefinically or acetylenically unsaturated epoxide
and subsequently
with a mixture, containing short chained, preferably hydroxy functionalized, carboxylic acids and long chained, preferably hydroxy free, carboxylic acids, and optionally afterwards with primary or secondary amines, wherein optionally the carboxylic acids can be obtained by partial esterification or amidation of carboxylic acid anhydrides with corresponding alcohols or amines,
(g) a SiH functionalized polysiloxane is reacted with
one or more than one monofunctionally unsaturated alkyne and one or more than one monofunctional olefinically or acetylenically unsaturated epoxide
and subsequently
with long chained, preferably hydroxy free, carboxylic acids, and optionally afterwards with primary or secondary amines, wherein optionally the carboxylic acids can be obtained by partial esterification or amidation of carboxylic acid anhydrides with corresponding alcohols or amines,
(h) a SiH functionalized polysiloxane is reacted with
one or more than one monofunctionally unsaturated alkyne or alkene and one or more than one monofunctional olefinically or acetylenically unsaturated epoxide and one or more than one olefinically or acetylenically unsaturated fatty acid ester
and subsequently
with a mixture, containing short chained, preferably hydroxy functionalized, carboxylic acids and long chained, preferably hydroxy free, carboxylic acids, and optionally afterwards with primary or secondary amines, wherein optionally the carboxylic acids can be obtained by partial esterification or amidation of carboxylic acid anhydrides with corresponding alcohols or amines,
(i) a SiH functionalized polysiloxane is reacted with
one or more than one monofunctional olefinically or acetylenically unsaturated epoxide and one or more than one olefinically or acetylenically unsaturated fatty acid ester
and subsequently
with a mixture, containing short chained, preferably hydroxy functionalized, carboxylic acids and long chained, preferably hydroxy free, carboxylic acids, and optionally afterwards with primary or secondary amines, wherein optionally the carboxylic acids can be obtained by partial esterification or amidation of carboxylic acid anhydrides with corresponding alcohols or amines,
(j) a SiH functionalized polysiloxane is reacted with
one or more than one monofunctionally unsaturated alkyne or alkene and one or more than one monofunctional olefinically or acetylenically unsaturated epoxide and one or more than one olefinically or acetylenically unsaturated fatty acid ester
and subsequently
with short chained, preferably hydroxy functionalized, carboxylic acids, and optionally afterwards with primary or secondary amines, wherein optionally the carboxylic acids can be obtained by partial esterification or amidation of carboxylic acid anhydrides with corresponding alcohols or amines,
(k) a SiH functionalized polysiloxane is reacted with
one or more than one monofunctional olefinically or acetylenically unsaturated epoxide and one or more than one olefinically or acetylenically unsaturated fatty acid ester
and subsequently
with short chained, preferably hydroxy functionalized, carboxylic acids, and optionally afterwards with primary or secondary amines, wherein optionally the carboxylic acids can be obtained by partial esterification or amidation of carboxylic acid anhydrides with corresponding alcohols or amines,
(l) a SiH functionalized polysiloxane is reacted with
one or more than one monofunctionally unsaturated alkyne or alkene and one or more than one monofunctional olefinically or acetylenically unsaturated epoxide and one or more than one olefinically or acetylenically unsaturated fatty acid ester
and subsequently
with long chained, preferably hydroxy free, carboxylic acids, and optionally afterwards with primary or secondary amines, wherein optionally the carboxylic acids can be obtained by partial esterification or amidation of carboxylic acid anhydrides with corresponding alcohols or amines,
(m) a SiH functionalized polysiloxane is reacted with
one or more than one monofunctionally unsaturated alkyne or alkene and one or more than one monofunctional olefinically unsaturated epoxide and one or more than one acetylenically unsaturated fatty acid ester
and subsequently
with long chained, preferably hydroxy free, carboxylic acids, and optionally afterwards with primary or secondary amines, wherein optionally the carboxylic acids can be obtained by partial esterification or amidation of carboxylic acid anhydrides with corresponding alcohols or amines,
(n) a SiH functionalized polysiloxane is reacted with
one or more than one monofunctional acetylenically unsaturated epoxide and one or more than one acetylenically or olefinically unsaturated fatty acid ester
and subsequently
with long chained, preferably hydroxy free, carboxylic acids, and optionally afterwards with primary or secondary amines, wherein optionally the carboxylic acids can be obtained by partial esterification or amidation of carboxylic acid anhydrides with corresponding alcohols or amines,
(o) a SiH functionalized polysiloxane is reacted with
one or more than one monofunctional olefinically unsaturated epoxide and one or more than one acetylenically unsaturated fatty acid ester
and subsequently
with long chained, preferably hydroxy free, carboxylic acids, and optionally afterwards with primary or secondary amines, wherein optionally the carboxylic acids can be obtained by partial esterification or amidation of carboxylic acid anhydrides with corresponding alcohols or amines,
(p) an aminofunctional polysiloxane is reacted with short chained and/or long chained carboxylic acid esters, lactones, carboxylic acid halides or carboxylic acid silyl esters
(q) an aminofunctional polysiloxane is reacted with short chained and/or long chained alkyl or aryl substituted carbonates
(r) an aminofunctional polysiloxane is reacted with short chained and/or long chained alkyl substituted epoxides Starting point for the synthesis are in particular SiH-functional polysiloxanes, wherein hydrogen is formally replaced by substituents corresponding to $R^9$.

Insofar as they are not commercially available, these SiH-functional polysiloxanes can be produced by known processes, e.g. by equilibrating (Silicone, Chemie and Technologie, Vulkan-Verlag Essen 1989, p. 82-84).

It is within the bounds of the invention to use several different SiH-functional polysiloxanes.

In one embodiment epoxy groups are first introduced from the SiH-functional poly-siloxanes, preferably by hydrosilylation reaction with olefinically or acetylenically unsaturated epoxy compounds.

Thus, preferred epoxy functional precursor structures are formed

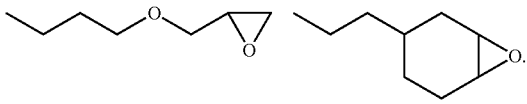

Alternatively, appropriate aminosiloxanes can be produced by known alkaline catalysed equilibrating reactions, which for example comprise
—CH$_2$CH$_2$CH$_2$NH$_2$
—CH$_2$CH$_2$CH$_2$NHCH$_3$
—CH$_2$CH$_2$CH$_2$NHCH$_2$CH$_2$NH$_2$
substituents on the D-siloxane units (Silicone, Chemie and Technologie, Vulkan Verlag Essen 1989, p. 28-30). These reactively functionalised intermediary siloxane stages can be converted in a further step into the polysiloxane compounds according to the invention, for example by reaction with carboxylic acids under formation of amines, with epoxy functional compounds under formation of amino alcohols or with hydroxylated alcohols, also under formation of amino alcohols.

For introducing of the hydrophilic elements $R^{91}$ the aforementioned reactively functionalised intermediate stages are, for example, reacted with
hydroxyl groups comprising carboxylic acids or
at least one carboxylic acid group and at least one hydroxyl group comprising
esters or
lactones.

The esterification of epoxides with carboxylic acids, if necessary in the presence of catalysts such as e.g. tertiary amines, is known (E. Sung, W. Umbach, H. Baumann, Fette Seifen Anstrichmittel 73, 1971, p. 88).

The amide formation by the reaction of amines with esters and lactones is known as such (Organikum, VEB Deutscher Verlag der Wissenschaften, 17th Edition, 1988, p. 408-412; DE OS 4318536 Example 22).

The hydroxyl groups comprising carboxylic acids are monohydroxy and polyhydroxy carboxylic acids, for example glycolic acid, lactic acid, γ-hydroxy butyric acid, 2,3-dihydroxy propionic acid, α,β-dihydroxy butyric acid, α,γ-dihydroxy butyric acid, gluconic acid, glucopyranosylarabinoeic acid. The use of very long-chained hydroxy carboxylic acids, for example ricinoleic acid is possible, but less preferred.

It lies within the bounds of the invention to use the acids for carrying out the reaction as an acid or also as an ester, particularly methylester or lactone, for example γ-butyrolactone, gluconic acid lactone and glucopyranosylarabinoeic acid lactone. The use of very long-chained lactones, for example 5-dodecanolide, is possible, but less preferred.

The use of acids with more than one carboxylic acid function, for example mucic acid or its epimer glucaric acid, is possible, but less preferred. By using difunctional carboxylic acids a specific increase of the molecular weight can be achieved by partial crosslinking.

Alternatively, at least one carboxylic acid group and esters comprising at least one hydroxyl group can be used for the introduction of the hydrophilic residue $R^{91}$. A preferred embodiment includes monoesters of dicarboxylic acids. Examples of dicarboxylic acids are oxalic acid, succinic acid, maleic acid, fumaric acid, phthalic acid, terephthalic acid. It lies within the bounds of the invention to esterify the carboxylic acids in the form of their anhydrides. The alcohols used for esterification are at least dihydroxy-functional alcohols with a chain length of ≥C3 atoms. Examples of alcohols are 1,2-propane diol, 1,3-propane diol, glycerol, pentaerythrol and sorbitol.

The group $R^{91}$ can also be synthesized via a hydrosilylation reaction of a polyhydric monoether, wherein the rest of the hydroxy groups are blocked by a protective group, such as a ketal group or trimethylsilyl group. Preferred precursors are monoallylether, e.g. of glycerol or polyglycerols.

It lies within the bounds of the invention to esterify the alcohols, in the form of their epoxides, for example propylene oxide, with the acids.

The use of tri- and higher functional carboxylic acids is possible, but less preferred. An example is trimellitic acid, which can be converted into a non-carboxylic acid diester structure particularly starting from trimellitic acid anhydridic acid chloride. Another example is pyromellitic acid dianhydride, which preferably forms a dicarboxylic acid diester structure. As already discussed, an increase of the molecular weight via partial crosslinking can be achieved by using difunctional carboxylic acids.

For introducing the hydrophilic elements $R^{91}$ the aforementioned reactively functionalised intermediate stages, particularly epoxy functionalised intermediate stages, can be partially reacted with for example
hydroxyl groups comprising primary or secondary amines or
at least one primary or secondary amino group and at least one hydroxyl group comprising amino amides.

The hydroxyl groups containing primary or secondary amines are for example ethanol amine, diethanol amine, 1-amino-(2-hydroxy) propane, 1-amino-(3-hydroxy), propane, 1-amino-2,3-dihydroxy propane, glucamine, N-methyl-glucamine.

The amino amides preferably are reaction products of primary-secondary amines with lactones, particularly hydroxylated lactones. Examples of preferred primary-secondary amines are H$_2$NCH$_2$CH$_2$NHCH$_2$CH$_2$NH$_2$ and H$_2$NCH$_2$CH$_2$CH$_2$NHCH$_2$CH$_2$CH$_2$NH$_2$. Examples of preferred lactones are γ-butyrolactone, δ-gluconolactone, glucopyranosylarabinoeic acid lactone. The production of such complex amino amides is defined in DE 4318536, Examples 11 to 18.

For introducing the lipophilic element $R^{92}$ the afore-mentioned reactively functionalised intermediate stages are reacted preferably with carboxylic acid or at least one carboxylic acid group comprising esters.

In the context of the invention fatty acids are understood to be monocarboxylic functional carboxylic acids. Examples of suitable fatty acids are acetic acids, caproic acid, 2-ethylcaproic acid, lauric acid, tetralauric acid, hexylauric acid, octalauric acid, unlauric acid, oleic acid, linoleic acid, linolenic acid.

For the introduction of the lipophilic residues $R^{92}$ preferably monocarboxylic functional carboxylic acids with ≥C10 atoms are used, as these have a particularly strong bonding capacity the solubility in the oil phase.

For the introduction of the hydrophilic residues $R^{91}$ preferably mono or polycarboxylic functional carboxylic acids with <C10 atoms or hydroxy functional carboxylic acids are used.

The carboxylic acids used as precursors for $R^{92}$ or $R^{91}$ can be introduced either over a reaction with an epoxide group linked to a siloxy group or over a hydrosilylation reaction with esters comprising carbon double or triple bonds and SiH-groups. It is preferred to use allylesters of monocarboxylic carboxylic acids. It is within the bounds of the invention to use the acids for carrying out the reaction as an acid or also as an ester, particularly methyl ester, for example oleic acid methyl ester.

The use of acids with more than one carboxylic acid function, for example lauric diacid or dodecenyl succinic acid and their anhydrides respectively, is possible, but less preferred. The use of difunctional carboxylic acids can specifically achieve an increase of the molecular weight via partial crosslinking.

Alternatively, at least one carboxylic group comprising ester can be used for the introduction of the residue $R^9$.

They are monoesters of dicarboxylic acids in a preferred embodiment. Examples of dicarboxylic acids are oxalic acid, succinic acid, maleic acid, fumaric acid, phthalic acid, terephthalic acid. It is within the bounds of the invention to esterify the carboxylic acids in the form of their anhydrides. The alcohols used for esterification are preferably monohydroxy functional alcohols. Examples of alcohols are ethanol, 2-propanol, 2-ethylhexanol, dodecanol, undecenol, isotridecanol, hexadecanol, oleyl alcohol, octadecanol, mono- and oligopropoxylates of monohydroxy functional alcohols, $HOCH_2CH_2(CF_2)_5CF_3$ and $HO(CH_2)_6Si(CH_3)_3$.

It lies within the bounds of the invention to esterify the alcohols in the form of their epoxides, for example dodecene oxide, with the diacids.

The use of tri- and higher functional carboxylic acids is possible, but less preferred. An example is trimellitic acid, which can, starting from trimellitic acid anhydride acid chloride, be converted into a monocarboxylic diester structure. Another example is pyromellitic acid dianhydride, which preferably forms a dicarboxylic acid diester structure. As already discussed, a specific increase in the molecular weight can be achieved by the use of difunctional carboxylic acids via partial crosslinking.

It lies within the bounds of the invention to react the respective epoxy or amino functional polysiloxane intermediate stages with one or more hydrophilic component and/or one or more lipophilic component for the introduction of the groups $R^9$.

It is preferred in an embodiment of the invention to react the respective epoxy or amino functional siloxane intermediate stages with a mixture of the hydrophilic and lipophilic acid components. In a further preferred embodiment of the invention, the respective epoxy or amino functional siloxane intermediate stages are first of all reacted with the hydrophilic acid components and then the lipophilic acid components are added to the reaction preparation. The reverse order, that is first the reaction with the lipophilic acid component and then the addition of the hydrophilic acid component, is also possible.

The application of the afore-mentioned concepts relating to several hydrophilic and/or lipophilic acid components various addition sequences leads to chemically differently composed component parts which finally go into the end product.

The molar ratio Σ of epoxide respectively amine:Σ the acid component amounts to 1:1 to 1:2, preferably 1:1 to 1:1.5, especially 1:1 to 1:1.1.

In order to regulate the characteristics of the polysiloxane copolymers according to the invention as W/O-emulsifiers, the ratios of the individual structural elements to one another is significant. These can, within the bounds of the invention, be adapted to the chemical structure of the oil to be emulsified and the intended proportion of water phase:oil phase.

An increase in the proportion of the conventional "non-modified" siloxane units tends to result in, for example, a better compatibility with the siloxane-based oil phases.

An increase in the proportion of the hydrophilic units tends to result in, for example, a better compatibility with the water phase.

An increase in the proportion of lipophilic units tends to result in, for example, a better compatibility with hydrocarbon-based oil phases.

It lies within the bounds of the invention to carry out the reactions for the production of the polysiloxane compounds in accordance with the invention without solvents or in the presence of solvents. Suitable solvents are, for example, esters or ester-comprising mixtures, such as ethyl acetate, butyl acetate, methoxypropyl acetate, ester aromatic substances, such as e.g. acetic acid esters of dicyclopentadiene, ether or ether-comprising mixtures, such as dibutyl ether, ether aromatic substances, such as e.g. methyl ether of dicyclopentadiene, alcohols, such as ethanol, e-propanol, propylene glycol and glycerol. The optional choice of a solvent and its required quantity are inter alia dependent on the structure of the acid component and the intended application purpose. Thus, it can be advantageous to already perform the synthesis in a solvent, which is, for example, a component of the final W/O-formulation.

The reactions are preferably carried out in a temperature range between room temperature and 180° C., preferably room temperature and 150° C., most preferably 50° C. and 150° C.

The reaction times are determined by the complete reaction of epoxy and amino groups. These can be easily observed by suitable methods (IR, NMR, Titration).

Preferred Applications

By changing the ratios of $R^{91}$ to $R^{92}$ it is possible to alter the solubility characteristics considerably. If the ratio $R^{91}:R^{92}$ is the same or greater than 1 in particular effects such as reduced dynamic friction and antistatic characteristics on hydrophobic surfaces can be achieved.

These more hydrophilic compounds feature, in comparison to pure polydimethyl-siloxanes, an improved solubility in polar solvents, such as alcohols, other oxygen-, sulphur- and nitrogen-comprising hydrocarbons.

A further preferred embodiment of the invention relates to the use of the hydrophilic/lipophilic modified polysiloxane compounds according to the invention for the production of viscosity regulators, antistatic agents, mixture components for silicone rubbers which can be crosslinked to elastomers, either by peroxides or by hydrosilylation (platinum catalyst) and lead in that case to the modification of surface characteristics, the modification of the diffusion of gases, liquids, etc., modify the swelling characteristics of the silicone elastomers e.g. compared to water, respectively.

In particular, the use as an additive for the hydrophilisation of the surfaces of polydimethylsiloxane elastomers in general, or as a viscosity regulator in non-crosslinked silicic acid-comprising silicone rubbers is preferred. Here silicone rubbers mean in particular low-viscosity moulding or sealing masses known as Room-Temperature-Vulcanizing (RTV) 1- or 2-component rubbers. For these RTV 1-C or 2-V rubbers the adjustment of high or low flow limits depending on the use, is desired. The organo-modified polydimethylsiloxane according to the invention is applied in amounts of from 0.5 to 15 wt.-%—relative to the silicone rubbers during the production of the rubber composition or to the surface of the elastomer.

They can also be applied onto the surface as lubricants by immersion, pouring or spreading and can be partially removed again by rubbing or rinsing after intended use or setting up.

A further preferred embodiment of the invention relates to the use of the hydrophilic/lipophilic modified polysiloxane compounds according to the invention for the production of modifying agents for thermoplastic plastic materials such as polyolefins, polyamides, polyurethanes, poly(meth)acrylates and polycarbonates. This includes, in particular, the use as or production of low temperature impact resistant modifying agents.

For this the polysiloxane compounds themselves can be used directly as modifying agents or, however, also be prepared in advance by mixing, compounding or master-batching production in a suitable form.

A further use of the copolymers according to the invention includes coatings, such as anti-fouling, non-stick coatings, body tissue compatible coatings and materials.

Further uses include anti-fogging coatings or the precursors for the production of these for headlight glass (inner surface), panes for residential buildings, for automobiles or medical equipment as well as additives for cleaning agents, detergents or preservative agents, as an additive for toiletries, as a coating agent for wood, paper and cardboard, as a mould release agent, as a biocompatible material for medicinal uses such as contact lenses, as a coating agent for textile fibres or textile fabrics, as a coating agent for natural materials such as e.g. leather and furs or fleeces.

The hydrophilic/lipophilic modified polysiloxanes can also serve as cosmetics, toiletries, paint additives, additives in detergents, defoaming formulations and in textile processing.

In a preferred use the hydrophilic/lipophilic modified polysiloxanes with $R^{91}:R^{92}<1$ are applied for the defoaming of diesel oils and diesel fuels respectively, wherein the concentration of silicon in diesel oil is less than 5 ppm, more preferably less than 2 ppm.

A further preferred use is the application of the hydrophilic/lipophilic modified polysiloxanes with $R^{91}:R^{92}<1$ as a foam stabiliser in cold or warm hardening polyurethane hard or flexible foams, preferably in amounts of from 0.5 to 5 wt.-%, more preferably 1 to 3 wt.-% per applied polyol component with additional expanding agents whose boiling points lie between −60 and 50° C., such as, in particular, cyclopentane, iso-pentane, and/or iso-butane. The ratio of (g+f2):f1 is preferably 1 to 15:1, more preferably 2 to 9:1. The index f2 of the lipophilic units is 0 to 60, more preferably 1-10. The sum of the siloxy units g+f2+f1 is 15 to 200, more preferably, 30 to 150 measured as average polymerisation degree $P_n$ on the basis of the mean average number $M_n$ from a gel chromatic molar weight determination (GPC). Linear polyorgano-siloxanes with siloxy units, which are indicated with g, f1, f2 and k, are preferably used. In another preferred use of the hydrophilic/lipophilic modified polysiloxanes with $R^{91}:R^{92}<1$ is the defoaming of diesel oils or hydrocarbon fuels respectively, wherein the concentration of silicon in diesel oil is less than 5 ppm, more preferably less than 2 ppm.

These uses comprise the production of softening agents for textile fibres for the treatment of textile fibres before, during and after washing, of agents for the modification of natural and synthetic fibres, such as for example hair, cotton fibres and synthetic fibres, such as polyester fibres and polyamide fibres, as well as blended fabrics, finishing agents for textiles, as well as formulations comprising detergents, such as detergents or cleaning agents.

The preferred amounts in this case are 0.1 to 5 wt.-%, 0.3 to 3 wt.-%, corresponding to the fibre mass.

The preferred field of application for the polysiloxanes according to the invention is the use as an emulsifier for the production of water-in-oil emulsions.

In an other preferred embodiment of the invention the hydrophilic/lipophilic modified polyorganosiloxanes with $R^{91}:R^{92}<1$ of this invention are used as adjuvant in pesticides, agriculture, horticulture, turf, ornamental and forestry or emulsifier in compositions used therefore. The preferred siloxanes for this use are linear polyorganosiloxanes with siloxy with M and D-units, which are indicated with g, f1, f2, j and k, whereby j+k=2 and g, f1, f2=1-100 in average. Preferably each of the groups $R^{91}$ and $R^{92}$ are present and the molar ratio of the siloxy units comprising hydrophilic $R^{91}$ to lipophilic $R^{92}$ groups is <1. These siloxane compounds preferably showing a low HLB-value<8 improve dispersibility of active materials and stabilize the emulsions when diluted with more water.

Many pesticide applications require the addition of an adjuvant to the spray mixture to provide wetting and spreading on foliar surfaces. Often that adjuvant is a surfactant, which can perform a variety of functions, such as increasing spray droplet retention on difficult to wet leaf surfaces, enhance spreading to improve spray coverage, or to provide penetration of the herbicide into the plant cuticle. These adjuvants are provided either as a tank-side additive or used as a component in pesticide formulations.

Typical uses for pesticides include agricultural, horticultural, turf, ornamental, home and garden, veterinary and forestry applications.

The pesticidal compositions of the present invention also include at least one pesticide, where the compounds of the present invention are present at an amount sufficient to deliver between 0.005% and 2% to the final use concentration, either as a concentrate or diluted in a tank mix. Optionally the pesticidal composition may include excipients, co-surfactants, solvents, foam control agents, deposition aids, drift retardants, biologicals, micronutrients, fertilizers and the like. The term pesticide means any compound used to destroy pests, e.g., rodenticides, insecticides, miticides, fungicides, and herbicides. Illustrative examples of pesticides which can be employed include, but are not limited to, growth regulators, photosynthesis inhibitors, pigment inhibitors, mitotic disrupters, lipid biosynthesis inhibitors, cell wall inhibitors, and cell membrane disrupters. The amount of pesticide employed in compositions of the invention varies with the type of pesticide employed. More specific examples of pesticide compounds that can be used with the compounds or compositions of the invention are, but not limited to, herbicides and growth regulators, such as: phenoxy acetic acids, phenoxy propionic acids, phenoxy butyric acids, benzoic acids, triazines and s-triazines, substituted ureas, uracils, bentazon, desmedipham, methazole, phenmedipham, pyridate, amitrole, clomazone, fluridone, norflurazone, dinitroanilines, isopropalin, oryzalin, pendimethalin, prodiamine, trifluralin, glyphosate, sulfonylureas, imidazolinones, clethodim, diclofop-methyl, fenoxaprop-ethyl, fluazifop-p-butyl, haloxyfop-methyl, quizalofop, sethoxydim, dichlobenil, isoxaben, and bipyridylium compounds.

Fungicide compositions that can be used with the compounds of the present invention include, but are not limited to, aldimorph, tridemorph, dodemorph, dimethomorph; flusilazol, azaconazole, cyproconazole, epoxiconazole, furconazole, propiconazole, tebuconazole and the like; imazalil, thiophanate, benomyl carbendazim, chlorothialonil, dicloran, trifloxystrobin, fluoxystrobin, dimoxystrobin, azoxystrobin, furcaranil, prochloraz, flusulfamide, famoxadone, captan, maneb, mancozeb, dodicin, dodine, and metalaxyl.

Insecticide, larvacide, miticide and ovacide compounds that can be used with the composition of the present invention, but not limited to, *Bacillus Thuringiensis*, spinosad, abamectin, doramectin, lepimectin, pyrethrins, carbaryl, primicarb, aldicarb, methomyl, amitraz, boric acid, chlordimeform, novaluron, bistrifluoron, triflumuron, diflubenzuron, imidacloprid, diazinon, acephate, endosulfan, kelevan, dimethoate, azinphos-ethyl, azinphos-methyl, izoxathion, chlorpyrifos, clofentezine, lambda-cyhalothrin, permethrin, bifenthrin, cypermethrin and the like.

The pesticide may be a liquid or a solid. If a solid, it is preferable that it is soluble in a solvent, or the compounds of the present invention, prior to application, and the compounds of the invention may act as a solvent, or surfactant for such solubility or additional surfactants may perform this function.

Agricultural Excipients:

Buffers, preservatives, carriers and other standard excipients known in the art also may include the compounds of the invention.

Solvents may also be included in compositions comprising the compounds of the present invention. These solvents are in a liquid state at room temperature (25° C.). Examples include water, alcohols, aromatic solvents, oils (i.e. mineral oil, vegetable oil, silicone oil, and so forth), lower alkyl esters of vegetable oils, fatty acids, ketones, glycols, polyethylene glycols, diols, paraffinics, and so forth. Particular solvents would be 2,2,4-trimethyl, 1,3-pentanediol and alkoxylated (especially ethoxylated) versions thereof as illustrated in U.S. Pat. No. 5,674,832 herein incorporated by reference, or N-methyl-pyrrolidone.

Co-Surfactants:

Moreover, co-surfactants, which have short chain hydrophobes that do not interfere with superspreading as described in U.S. Pat. Nos. 5,558,806; 5,104,647; and 6,221,811 are herein included by reference.

The co-surfactants useful herein include nonionic, cationic, anionic, amphoteric, zwitterionic, polymeric surfactants, or any mixture thereof. Surfactants are typically hydrocarbon based, silicone based or fluorocarbon based.

Useful surfactants include alkoxylates, especially ethoxylates, containing block copolymers including copolymers of ethylene oxide, propylene oxide, butylene oxide, and mixtures thereof; alkylarylalkoxylates, especially ethoxylates or propoxylates and their derivatives including alkyl phenol ethoxylate; arylarylalkoxylates, especially ethoxylates or propoxylates, and their derivatives; amine alkoxylates, especially amine ethoxylates; fatty acid alkoxylates; fatty alcohol alkoxylates; alkyl sulfonates; alkyl benzene and alkyl naphthalene sulfonates; sulfated fatty alcohols, amines or acid amides; acid esters of sodium isethionate; esters of sodium sulfosuccinate; sulfated or sulfonated fatty acid esters; petroleum sulfonates; N-acyl sarcosinates; alkyl polyglycosides; alkyl ethoxylated amines; and so forth.

Specific examples include alkyl acetylenic diols (SURFONYL® from Air Products), pyrrilodone based surfactants (e.g., SURFADON®-LP 100—ISP), 2-ethyl hexyl sulfate, isodecyl alcohol ethoxylates (e.g. RHODASURF® DA 530—Rhodia), ethylene diamine alkoxylates (TETRONICS®—BASF), and ethylene oxide/propylene oxide copolymers (PLURONICS®—BASF) and Gemini type surfactants (Rhodia).

Preferred surfactants include ethylene oxide/propylene oxide copolymers (EO/PO); amine ethoxylates; alkyl polyglycosides; oxo-tridecyl alcohol ethoxylates, and so forth.

Use in Coatings and Paints:

In a further preferred embodiment of the invention the hydrophilic/lipophilic modified polyorganosiloxanes of this invention are use in coating compositions. Typically coating formulations may include the compounds of the present invention as a wetting agent or surfactant for the purpose of emulsification, compatibilization of components, leveling, flow enhancement, deairing and the reduction of surface defects. Additionally, the compounds of the invention may provide improvements in the cured or dry film, such as improved abrasion resistance, antiblocking, hydrophilic, and hydrophobic properties. Coatings formulations may exists as, solvent-borne coatings, water-borne coatings and powder coatings.

The coatings components may be employed as: Architecture coatings; OEM-product coatings such as automotive coatings and coil coatings; special purpose coatings such as industrial maintenance coatings and marine coatings;

Typical resins include polymers of polyesters, alkyds, acrylics, epoxies, and polyurethanes.

A further preferred use is the application of hydrophilic/lipophilic modified polysiloxanes with predominantly hydrophilic characteristics $R^{91}:R^{92}>1$ as an additive for the hydrophilisation, improved wettability and antistatic finishing of thermoplastic and elastomeric surfaces. The preferred amounts in this case are 0.2 to 15 wt.-%, 0.5 to 10 wt.-% relative to the thermoplastic or elastomeric composition. Another preferred application of the hydrophilic/lipophilic modified polysiloxanes is the use in the heat sensitized coagulation of rubber latex for the manufacture of e.g. gloves, condomes, balloons other latex based articles, whereby the solubility in the latex emulsion decreases when heated up to >35° C.; it prevents premature coagulation at room temperature.

Another preferred application is the use as demulsifiers in the oil and gas industry for faster and better separation of crude oil and water, as additive for anti-blocking, anti-fogging in order to prevent water droplets onto surfaces, mar resistance, as lubricant or lubricating additive, as tissue softeners or in tissue softener composition as self-emulsifying alklylene oxide-free softener or as shear stable emulsifier in textile treatment formulations, as foam stabilizers for aqueous foams in detergents, dishwashing liquids and in general-purpose cleaners, as additives for hydrophilisation of plastic and thermoplastic or elastomer surfaces and the improved wettability of thermoplastic or elastomeric surfaces.

Production of Water-in-Oil Emulsions (W/O-Emulsions):

The preferred ester units in accordance with the invention comprising polysiloxanes can in this case be used hereby singly as well as in combination of various structures and, furthermore, in combination with other emulsifiers. W/O-emulsifiers generally comprise an external less polar phase, which hereinafter is referred to as the oil phase, an internal polar phase, which hereinafter is called the aqueous phase and an emulsifier or emulsifiers. Various raw materials can be introduced into the polar respectively non-polar phase.

Water Phase

In this connection, the aqueous phase of the described W/O-emulsions can comprise water, alcohols and polyols such as for example glycerine and its ester, ethylene glycol, diethylene glycol and its ester, propylene glycol, dipropylene glycol, butylene glycol and its ester, ethanol, isopropanol and sorbitol as well as combinations thereof. Furthermore, soluble substances, such as for example salts, active substances, preservatives, inorganic and organic dyes, oxidants and pH-regulators can be introduced into the aqueous phase.

Emulsifiers

The following emulsifiers can be used together with the polysiloxane compounds according to the invention respectively combinations thereof. Emulsifiers comprising polyalkylene oxide groups can also be used in the process, wherein they can be applied in lesser amounts by using the polysiloxane compounds in accordance with the invention, or they can be completely dispensed with.

Anionic emulsifiers such as metal soaps are fatty acid salts of polyvalent metals, such as for example the stearates, myristates, laureates or oleates of magnesium, zinc and aluminium.

Amphoteric emulsifiers are phospholipids and proteins such as lecithin and lactoproteins.

Non-ionic emulsifiers such as fatty alcohols, absorption or ointment bases on the basis of different raw materials such as petroleum jelly, paraffin, mineral oil, beeswax, lanolin, cholesterol and alcohols with a high molecular weight and esters thereof, lecithin and eucerite, (purified wool wax alcohol) are produced, wool wax alcohol and its fractions (in particular cholesterol), partial esters of multivalent alcohols with higher fatty acids, sterols as well as oleates, ricinolates and lanolates of sorbitane, pentaerythrit, glycerine and polyglycerine.

Silicone emulsifiers such as PEG-x/PPG-y dimethicone (x=0-100, y=0-100, x+y≥1), alkyl PEG-x/PPG-y dimethicone (alkyl=linear and branched alkyl or aryl residues with 2-50 carbon atoms, x=0-100, y=0-100, x+y≥1), poly-glyceryl-x disiloxane dimethicone (x=2-10), polyglyceryl-x polydimethylsiloxyethyl dimethicone (x=2-10) and alkyl polyglyceryl-x polydimethylsiloxyethyl dimethicone Alkyl=linear and branched alkyl respectively aryl residues with 2-50 carbon atoms, x=2-10).

Particularly suitable emulsifiers, which can either be used alone or together in any combination with the polysiloxanes in accordance with the invention, are glyceryl oleate, glyceryl isostearate, sorbitane trioleate, sorbitane sesquioleate, sorbitane sesquiisostearate, sorbitane oleate, sorbitane isostearate, methyl glucose dioleate, methyl glucose sesquistearate, dicocoyl pentaerythrityl distearyl citrate, pentaerythrityl tetralaurate, polyglyceryl-2 sesquioleate, polyglyceryl-2 sesquiisostearate, polyglyceryl-3 sesquioleate, polyglyceryl-3 sesquiisostearate, polyglyceryl-4 oleate, PEG-4 oleate, PEG-6 dioleate, PEG-5 soy sterol, Peg-7 hydrogenated castor oil, oleth-2, oleth-3, isosterareth-2, isostearyl diglyceryl succinate, trioleyl phosphate, calcium stearoyl lactylate, laurylmethicone copolyol and cetyl dimethicone copolyol.

Oil Phase

In this connection the oil phase can comprise an oil or, however, combinations of two or more oils and also further oil-compatible cosmetic raw materials. Oils, which are used in cosmetics differ in their polarity. These can, according to the literature (Cosmetology—Theory and Practice; Volume 3, page 31, Table 10.2; Editors: K. Schrader, A. Domsch; Verlag für chemische Industrie, 2005), be described by their surface tension (also defined as polarity index). A particular characteristic of the polysiloxane compounds according to the invention is that, in this connection, they are capable of stabilising emulsions with a great range of oil polarities. In this connection the preferred oil polarities represented by the polarity index lie in a range of between 4 and 55 mN/m, with the range between 13 and 39 mN/m being particularly preferred. In this connection it is self-evident that the values of the oil polarities lie in the preferred or more preferred range and can be achieved by mixing or blending two or more components. The following materials are named as possible components for the oil phase, by way of example but not limiting, wherein the materials can be introduced singly or in combinations of several components. Triglycerides are, for example, avocado oil, peanut oil, hydrogenated peanut oil, oat oil, mink oil, olive oil, castor oil, hydrogenated caster oil, shea butter oil, soy oil, sunflower oil, sesame oil, peach stone oil, wheat germ oil, macadamia nut oil and oenothera biennis oil.

Silicones such as volatile linear and cyclic polydimethyl siloxane (hexamethyl disiloxane, ethyl-, propyl and butyl disiloxane, diethyl-, dipropyl- and dibutyl disiloxane, octamethyl disiloxane, octamethyl trisiloxane, pentamethyl tetrasiloxane, dodecamethyl pentasiloxane, various ethyl and diethyltrisiloxanes, various propyl- and dipropyl trisiloxanes, various butyl trisiloxanes, various pentyl trisiloxanes, various hexyl trisiloxanes, cyclotetrasiloxanes, cyclopentasiloxanes, cyclohexasiloxanes, cycloheptasiloxanes and further variations), dimethicone (viscosity 3-100 kPa·s at 25° C. as well as blends of the different viscosities and solutions of dimethicones in volatile silicones and hydrocarbons), phenyl modified silicones (phenyltrimethicones and phenyldimethicones with different viscosities as well as blends thereof), alkyl- and aryl modified silicones (caprylylmethicones, stearyl-, cetyl-, cetearyl-, C26-C28-alkyl C30-C45-alkyl methicones and dimethicones, phenylpropyldimethylsiloxysilicate), polyether modified silicones (INCI: PEG-x/PPG-y dimethicones), amino functional silicones (amo-dimethicones), fluoroalkyl modified silicones, silicone resins (trimethylsiloxysilicate, polymethylsilsesquioxanes, diisostearyl trimethylolpropane siloxysilicates and trifluoropropyl/trimethylsiloxysilicates), silicone acrylates (dimethicone PEG-8 Polyacrylates) and silicone elastomers and silicone crosspolymers (dimethicone/vinyl dimethicone crosspolymer, C30-C45-alkyl cetearyl dimethicone crosspolymer, cetearyl dimethicone crosspolymer, dimethicone crosspolymer, cetearyl dimethicone crosspolymer, dimethicone/PEG-10/15 crosspolymer, PEG-15/lauryl dimethicone crosspolymer, PEG-10/lauryl dimethicone crosspolymer, dimethicone/polyglycerine-3 crosspolymer, lauryl dimethicone/polyglycerine-3 crosspolymer and dimethicone/vinyltrimethyl siloxysilicate crosspolymer).

Hydrocarbons such as for example paraffin oils with various viscosities, petroleum jelly, paraffins (hard and soft), microcrystalline waxes, ozocerites, ceresin, squalenes, squalanes and volatile, linear and/or branched hydrocarbons with 5 to 20 carbon atoms.

Fatty alcohols as consistency regulators such as, for example, lauryl-, myristyl-cetyl-, oleyl- and stearyl alkohol, and mono- and diglycerides of fatty acids.

Natural waxes and fats and those based on natural products such as Japanese wax, lanolin, cocoa butter, cetyl palmitate, beeswax (natural and synthetic), carnauba wax, candelilla wax and jojoba oil.

Fatty acid esters of monoalcohols such as isopropyl myristates, isopropyl palmitates, isopropyl stearates, oleyl oleates, decyl oleates and cetearyl ethylhexanoates.

Stabilisers

A particularly important substance group for use in the external phase are so-called stabilisers, which can be very important for the production of stable emulsions. These substances are generally incorporated in the oil phase and form gel-like structures. Particularly suitable for this purpose are fatty alcohols such as e.g. lauryl-, myristyl-, cetyl-, oleyl- and stearyl alcohol, hydrocarbon and polymer gels such as e.g. vaseline and polyethyls, paraffin wax (microcrystalline wax), wax esters such as e.g. cetyl palmitate, beeswax and substitutes, carnuba wax and candelilla wax, lanolin, multivalent metal soaps of fatty acids such as e.g. zinc- and magnesium ricinoleate as well as alkaline earth lanolates, calcium- and magnesium soaps and stearate soaps of multivalent metals, bentonite and modified bentonite, EO-PO-block copolymers such as e.g. PEG-22/dodecyl glycol copolymer, PEG-40/dodecyl glycol copolymer, and poloxamer types from BASF, silicone waxes such as stearyl-, cetyl-, cetearyl-, C26-C28-alkyl, C30-C45-alkyl methicone and dimethicone and silicone elastomers and silicone crosspolymers such as e.g. dimethicone/vinyl dimethicone crosspolymer, C30-C45-alkyl cetearyl dimethicone crosspolymer, cetearyl dimethicone crosspolymer, dimethicone crosspolymer, cetearyl dimethicone crosspolymer, dimethicone/PEG-10/15 crosspolymer, PEG-15/lauryl dimethicone crosspolymer, PEG-10/lauryl dimethicone crosspolymer, dimethicone/polyglycerine-3 crosspolymer, lauryl dimethicone/polyglycerine-3 crosspolymer and dimethicone/vinyltrimethyl siloxysilicate crosspolymer.

Consistency Agents

Consistency agents are monovalent, primary alcohols with a carbon chain length of more than 4 C-atoms such as lauryl-, myristyl-, cetyl-, stearyl-, oleyl and cetyl alcohol as well as mixtures thereof, mono- and diglycerides of fatty acids, natural waxes and those based on a natural basis, such as Japanese wax (*Cera japonica*), lanolin, cocoa butter, cetyl palmitate, beeswax (white, bleached and synthetic), carnauba wax, candelilla wax and jojoba oil, fatty acid esters of monovalent alcohols such as isopropyl myristates, isopropyl palmitates, isopropyl stearates, oleyl oleates, decyl oleates and cetearyl ethylhexanoates, silicone waxes such as stearyl-, cetyl-, cetearyl-, C26-C28-alkyl, C30-C45-alkyl methicones and dimethicones and silicone elastomers and silicone crosspolymers such as e.g. dimethicones/vinyl dimethicone crosspolymer, C30-C45-alkyl cetearyl dimethicone crosspolymer, cetearyl dimethicone crosspolymer, dimethicone crosspolymer, cetearyl dimethicone crosspolymer, dimethicone/PEG-10/15 crosspolymer, PEG-15/lauryl dimethicone crosspolymer, PEG-10/lauryl dimethicone crosspolymer, dimethicone/polyglycerin-3 crosspolymer, lauryl dimethicone/polyglycerin-3 crosspolymer and dimethicone/vinyltrimethyl siloxysilicate crosspolymer.

Active Substances or Active Ingredients for Skincare Products

Suitable active ingredients for the production of W/O-emulsions with the polysiloxane compounds according to the invention are propolis or propolis wax, which is used because of its antimicrobial and antioxidative effect of the flavonoids comprised therein, Royal Jelly, which is suitable as a nurturing additive because of its high content of vitamins, amino acids, sugars, enzymes and biopeptin, collagen for stabilising the moisture of the stratum corneum, collagen hydrolysate for the improvement of skin and mucous membrane tolerance, elastin hydrolysate (hydrolysed elastin) alone or in combination with soluble collagen for the improvement of skin elasticity by hydration, phytosterols (avocado oil unsaponifiables, soy bean oil unsaponifiables) for a positive effect on the skin's connective tissue, vitamins such as vitamin A (retinol, retinyl acetate, retinyl palmitate and retinyl propionate) for the treatment and prevention of dry, rough, cornified and aging skin and atrophy of the perspiratory glands, beta-carotene which in the form of provitamin A exhibits the same effects as vitamin A, vitamin E (tocopherol, tocopherol acetate and tocopherol nicotinate) because of its antioxidative effect, improvement of the structure of the skin's surface, increase of the moisture-retaining properties of the corneum, the anti-inflammatory effect, acceleration of the epithelisation of superficial wounds, increase in the enzyme activity of the skin and boosting the blood circulation of the skin, pyridoxin or pyridoxin.HCl (vitamin B6) for the treatment of pellagra particularly in combination with essential fatty acids, niacin or niacin amides for the treatment of pellagra and of skin changes caused by deficiency symptoms, biotin (vitamin H) for the treatment of hair loss and anti-seborrhoic vitamin panthenol or d-panthenol and calcium panthenate for the improvement and increase of the moisture-retaining properties of the skin, for the inhibition of inflammation and itching, for the stimulation of epithelisation (accelerated healing of wounds), and for the improvement of the condition of damaged hair, vitamin C (ascorbic acid, sodium ascorbate and ascorbyl palmitate) because of its antioxidative effect and for the reduction of nitrosamine formation, essential fatty acids such as vitamin F (linoleic acid (and) linolenic acid (and) archidonic acid), vitamin-F-glycerol ester (glyceryl linoleic acid (and) glyceryl linolenic acid (and) glyceryl archidonic acid) and Vitamin-F-ethyl ester (ethyl linoleic acid (and) ethyl linolenic acid (and) ethyl archidonic acid) for the treatment of deficiency symptoms caused by a deficiency of linoleic acid such as dry, scaly skin rash, ceramide for the increase of moisture in the stratum corneum, anti-inflammatory substances such as bisabolol, camomile extracts, panthenol, glycyrrhizinic acid, witch hazel extract and certain peptides, ceratene-hardening substances which react with the proteins in the upper skin layers and thus to some extent seal it, such as formaldehyde or but also potassium aluminium sulfate, aluminium hydroxychloride, aluminium lactate, sodium-aluminium chlorohydroxy acetate and aluminium circonium tetrachlorohydrate-glycin complex which clog up the capillaries and also the perspiratory glands, antimicrobial substances, hyperemic substances which stimulate blood flow such as essential oils such as mountain pine oil, lavender, rosemary, juniper, horse chestnut extract, birch leaf extract, cornflower extract, ethyl acetate, nettle extract, camphor, menthol, nicotinic acid and derivatives, peppermint oil, eucalyptus oil and turpentine oil, liposomes for increasing skin penetration, glycolipids such as glycerol glyco-lipids, glycosphingolipids (neutral glycosphingolipids, sulfatides and gangliosides) and cerebrosides, lipoproteins and zinc oxide for anti-inflammation.

Micro Pigments

Micro pigments are also called UV-blockers. They are characterized in that they are insoluble in the oil and the aqueous phases of the emulsion and offer UV protection in that they reflect and disperse UV light independently of their size. In this connection attention must also be paid to the fact that that with a decreasing particle size the "whitening" effect of pigment residues on the skin are reduced. Mainly magnesium oxide, calcium carbonate, magnesium carbonate, bentonite, titanium dioxide and zinc oxide are used. Titanium dioxide and zinc oxide are the most frequently used, with the use of zinc oxide being favoured because of its additional anti-inflammatory effect. Of late organic compounds are also used as micro pigments. An example of this is bis-ethylhexyloxyphenyl triazine (Tinosorb S, Ciba). When using micro pigments it is important that they are easily dispersed in the incorporated phase in order to ensure an ideal covering of the skin, which then results in a more effective UV protection. For this the above-mentioned pigments are also used as surface-treatment materials or as pre-dispersions. For the production of dispersions all substances, which have already been mentioned above as components for the oil phase or the aqueous phase can be used. The surface treatment also results from these substances. Furthermore, for the surface treatment dimethicones, simethicone and cylic silicones and emulsions thereof, hexamethyldisiloxane, hexamethyldisiloxane, alkyl- and aryl-functionalised silicones with alkyl- or aryl residues comprising 2 to 50 C-atoms, methyl-, alkyl- and aryl-functionalised alkoxy or halogen silanes with alkyl- or aryl residues comprising 2 to 50 C-atoms or polyether-modified silicones are frequently used.

The micro pigments can be introduced singly or also in combinations. A combination with the following UV filters for optimising the UV protection is also possible.

UV Filters

UV filters are substances, which selectively absorb UVA and/or UVB radiation. Depending on the requirement profile, UV filters can be combined together and/or with micro pigments. Lists of suitable UV filters can be found in the "International Cosmetic Ingredient Dictionary and Handbook" Eleventh Edition 2006, Volume 3, page 2881 and "Cosmetology—Theory and Practice" Volume 3, pages 161-168; Editors: K. Schrader, A. Domsch; Verlag für Chemische Industrie, 2005.

Skin Tanning Agents

In this connection, examples of substances which tan the skin to be named are dihydroxyacetone, DHA and walnut extract.

Skin Bleaching Agents

Skin bleaching agents are used for the treatment of age spots or freckles. Active substances which can be used for producing cosmetic compositions with the aid of the polysiloxane compounds in accordance with the invention are hydroquinone, ascorbic acid, various peroxides, 5-hydroxy-2-(hydroxymethyl)-4H-pyran-4-on, 4-hydroxyphenyl-β-D-glucopyranosides and plant extracts. Further substances can be found in the "International Cosmetic Ingredient Dictionary and Handbook" Eleventh Edition 2006, Volume 3, page 2814.

Colorants and Dye Pigments

A list of suitable colorants and pigments can be found in the "International Cosmetic Ingredient Dictionary and Handbook" Eleventh Edition 2006, Volume 3, pages 2670-2677 and "Cosmetology—Theory and Practice" Volume 3, pages 222-223; Editors: K. Schrader, A. Domsch; Verlag für Chemische Industrie, 2005.

Further Fillers

This is understood to include particles and solids which influence light reflection and in this connection increase the proportion of the diffusely reflected light. Thus a soft focus effect is achieved which allows the skin to appear smoother and less wrinkled. Suitable additives are polymethyl silsesquioxanes, bornitride, nylon (Nylon-12), polyethylene (plastic powder), polyethylene/PTFE, dimethicone/vinyl dimethicone crosspolymer (and) lauroyl lysine, dimethicone/vinyl dimethicone crosspolymer (and) alumina, dimethicone/vinyl dimethicone crosspolymer (and) titanium dioxide, dimethicone/vinyl dimethicone crosspolymer, dimethicone/vinyl dimethicone crosspolymer (and) silica, polymethyl methacrylate, silica and silica silylate. These substances are also suitable for the absorption of sebum, which reduces skin shine.

Insect Protecting Agents

Suitable ingredients are inter alia ethyl butylacetylaminopropionate, diethyl toluamide and IR3535 Insect repellent by Merck.

Deodorants and Antiperspirants

Suitable ingredients for the production of antiperspirants with the polysiloxane compounds of the invention are fragrances, fragrance oils, triclosane, chlorhexidine, sodium hydrogen carbonate, clathrates such as zinc ricinolate and others, ion exchangers, triethylcitrate, o-acyl serine, acyl actylate, aluminium hydroxychloride, sodium aluminium chlorhydroxylactate, aluminium hydroxychloride with propylene glycol and circonium salts such as e.g. z.B. aluminium zirconium tetrachlorohydrex gly and aluminium circonium trichlorohydrex gly. Further antiperspirant active substances are mentioned in "Cosmetology—Theory and Practice" Volume 2, pages 268-269; Editors: K. Schrader, A. Domsch; Verlag für Chemische Industrie, 2005. A special form of antiperspirants are clear gels. These can be produced with the polysiloxane compounds according to the invention by matching the refraction indexes of the water and oil phases.

Ingredients for Hair Products

The polysiloxane compounds according to the invention are also suitable for the production of W/O-emulsions for hair care. In particular "leave-in" conditioners such as hair conditioners, hair gels, styling gels, hair forming agents, hair bleaching agents and hair colorants are to be mentioned here. The ingredients used in these compositions can be found in "Cosmetology—Theory and Practice" Volume 2; Editors: K. Schrader, A. Domsch; Verlag für Chemische Industrie, 2005.

Additives

Additives as ingredients for cosmetic formulations are defined in: A. Domsch, Die kosmetischen Präparate, Verlag für chem. Industrie, 4. Auflage, 1992; and in: Kosmetikjahrbuch 1995, Verlag für Chemische Industrie, 1995.

The following suitable additives are exemplary but, however, not limiting, as ingredients for the formulations: inorganic and organic acids, bases and buffers, salts, alcohols such as e.g. ethanol, isopropanol, ethylene glycol, polyethylene glycol, propylene glycol, polypropylene glycol, glycol ether and glycerine, thickeners, stabilisers for emulsions such as e.g. xanthan gum, emollients, preservatives, foam stabilisers, defoamers, pearlescents and opacifiers such as e.g. glycol distearate and titanium dioxide, collagen hydrolysate, keratin hydrolysate, silk hydrolysate, anti-dandruff agents such as e.g. zinc pyrithion, salicylic acid, selenium disulfide, sulphur and tar preparations, polymer emulsifiers, vitamins, dyes, UV filters, bentonites, perfume oils, fragrances, styling polymers, moisturizers, plant extracts and further natural and nature-identical raw materials.

The preferred use of the substances according to the invention is the use for the production of cosmetic compositions for the treatment of substances comprising keratin, such as the human skin or human hair. In this connection specific cosmetic formulations for the use of the polysiloxane compounds according to the invention are creams and lotions for face and body care, creams and lotions for UV radiation protection, self-tanners, skin lighteners and products for the treatment of hyperpigmentation such as age spots and freckles (skin whiteners), make-up removers, pigmented products such as mascaras, eyeliners, lipsticks and liquid make-up (liquid foundation), deodorants and antiperspirants such as e.g. gels, roll-ons, creams and emulsions, "leave-in" conditioners for the hair such as e.g. deep hair conditioners and cures and gels, hair styling products such as e.g. hair gels, styling mousses and creams and hair waxes, hair bleaching agents, hair forming agents, hair waving agents, hair colorants. The substances according to the invention are suitable for use as W/O-emulsions and can of course also be used in multiple emulsions.

A typical W/O-emulsion in accordance with the invention is produced in that the oil phase is provided and the emulsifier or the emulsifiers are added to the oil phase. Subsequently, the water phase is added by stirring. This process can, depending on the composition of the phases, be carried out cold as well as by heating. Subsequently, it is possible to follow up with a homogenisation step in order to possibly increase stability. With this procedure all the above-mentioned oil-compatible substances are dissolved or dispersed in the oil phase, whereas the hydrophilic substances are incorporated into the water or polar phase.

In this connection, a general W/O-emulsion according to the invention has the following composition in wt.-%:

| | |
|---|---|
| 0.1-20% | polysiloxanes according to the invention |
| 10-60% | oil phase |
| 0-10% | additives |
| 20-89.9% | water phase |

The following compositions were found to be particularly advantageous for the use of the polysiloxane compounds according to the invention in cosmetic formulations:

A typical composition for a W/O-cream according to the invention, which, however, does not limit the invention, comprises the following components in wt.-%:

| | |
|---|---|
| 0.2-10% | polysiloxane compounds according to the invention |
| 0-5% | Co-emulsifiers |
| 5-55% | oil or a combination of oils |
| 0-10% | stabilisers |
| 0-10% | consistency agents |
| 0-20% | active substances or active ingredients for skin care products |
| 0-10% | further fillers |
| 0-10% | adjuvants |
| up to 100% | completed with water. |

A specific composition of a W/O-cream, which, however, does not limit the invention, comprises the following components in wt.-%:

| | |
|---|---|
| 0.5-6% | polysiloxane compounds according to the invention |
| 0-3% | Co-emulsifiers |
| 10-40% | oil or a combination of oils |
| 0-5% | stabilisers |
| 0-5% | consistency agents |
| 0-20% | active substances or active ingredients for skin care products |
| 0-10% | further fillers |
| 0-10% | adjuvants |
| up to 100% | completed with water. |

A typical composition of a W/O-lotion according to the invention, which, however, does not limit the composition of the invention, comprises the following components in wt.-%:

| | |
|---|---|
| 0.2-10% | polysiloxane compounds according to the invention |
| 0-5% | Co-emulsifiers |
| 10-50% | oil or combination of oils |
| 0-10% | stabilisers |
| 0-10% | consistency agents |
| 0-20% | active substances or active ingredients for skin care products |
| 0-10% | further fillers |
| 0-10% | adjuvants |
| up to 100% | completed with water. |

A specific composition of a W/O-lotion, which, however, does not limit the invention, comprises the following components in wt.-%

| | |
|---|---|
| 0.5-6% | polysiloxane compounds according to the invention |
| 0-3% | Co-emulsifiers |
| 15-40% | oil or combination of oils |
| 0-5% | stabilisers |
| 0-5% | consistency agents |
| 0-20% | active substances or active ingredients for skin care products |
| 0-10% | further fillers |
| 0-10% | adjuvants |
| up to 100% | completed with water. |

A typical W/O-sunscreen cream composition according to the invention, which, however, does not limit the invention, comprises the following components in wt.-%:

| | |
|---|---|
| 0.2-10% | polysiloxane compounds according to the invention |
| 0-5% | Co-emulsifiers |
| 10-50% | oil or combination of oils |
| 0-10% | stabilisers |
| 0-10% | consistency agents |
| 0-20% | micro pigments |
| 0-20% | UV filters |
| 0-20% | active substances or active ingredients for skin care products |
| 0-10% | further fillers |
| 0-10% | adjuvants |
| up to 100% | completed with water. |

A specific W/O-sunscreen cream composition, which, however, does not limit the invention, comprises the following components in wt.-%:

| | |
|---|---|
| 0.5-6% | polysiloxane compounds in accordance with the invention |
| 0-3% | Co-emulsifiers |
| 10-40% | oil or combination of oils |
| 0-5% | stabilisers |
| 0-5% | consistency agents |
| 0-20% | micro pigments |
| 0-20% | UV filters |
| 0-20% | active substances or active ingredients for skin care products |
| 0-10% | further fillers |
| 0-10% | adjuvants |
| up to 100% | completed with water. |

A typical W/O-sunscreen lotion composition according to the invention, which, however, does not limit the invention, comprises the following components in wt.-%:

| | |
|---|---|
| 0.2-10% | polysiloxane compounds according to the invention |
| 0-5% | Co-emulsifiers |
| 10-45% | oil or combination of oils |
| 0-10% | stabilisers |

| | |
|---|---|
| 0-10% | consistency agents |
| 0-20% | micro pigments |
| 0-20% | UV filters |
| 0-20% | active substances or active ingredients for skin care products |
| 0-10% | further fillers |
| 0-10% | adjuvants |
| up to 100% | completed with water. |

A specific W/O-sunscreen lotion composition, which, however, does not limit the invention, comprises the following components in wt.-%:

| | |
|---|---|
| 0.5-6% | polysiloxane compounds according to the invention |
| 0-3% | Co-emulsifiers |
| 15-40% | oil or combination of oils |
| 0-5% | stabilisers |
| 0-5% | consistency agents |
| 0-20% | micro particles |
| 0-20% | UV filters |
| 0-20% | active substances or active ingredients for skin care products |
| 0-10% | further fillers |
| 0-10% | adjuvants |
| up to 100% | completed with water. |

A typical W/O-self-tanner composition according to the invention, which, however, does not limit the invention, comprises the following components in wt.-%:

| | |
|---|---|
| 0.2-10% | polysiloxane compounds according to the invention |
| 0-5% | Co-emulsifiers |
| 10-50% | oil or combination of oil |
| 0-10% | stabilisers |
| 0-10% | consistency agents |
| 0.5-15% | skin tanning agents |
| 0-10% | active substances or active ingredients for skin care products |
| 0-10% | further fillers |
| 0-10% | adjuvants |
| up to 100% | completed with water. |

A specific W/O-self-tanner composition, which, however, does not limit the invention, comprises the following components in wt.-%:

| | |
|---|---|
| 0.5-6% | polysiloxane compounds according to the invention |
| 0-3% | Co-emulsifiers |
| 10-40% | oil or combination of oils |
| 0-5% | stabilisers |
| 0-5% | consistency agents |
| 1-15% | skin tanning agents |
| 0-10% | active substances or active ingredients for skin care products |
| 0-10% | further fillers |
| 0-10% | adjuvants |
| up to 100% | completed with water. |

A typical W/O-skin brightener composition according to the invention, which, however, does not limit the invention, comprises the following components in wt.-%:

| | |
|---|---|
| 0.2-10% | polysiloxane compounds according to the invention |
| 0-5% | Co-emulsifiers |
| 10-50% | oil or combination of oils |
| 0-10% | stabilisers |
| 0-10% | consistency agents |
| 0.5-15% | skin bleaching agents |
| 0-10% | active substances or active ingredients for skin care products |
| 0-10% | further fillers |
| 0-10% | adjuvants |
| up to 100% | completed with water. |

A specific W/O-skin brightener composition, which, however, does not limit the invention, comprises the following components in wt.-%:

| | |
|---|---|
| 0.5-6% | polysiloxane compounds according to the invention |
| 0-3% | Co-emulsifiers |
| 10-40% | oil or combination of oils |
| 0-5% | stabilisers |
| 0-5% | consistency agents |
| 1-15% | skin bleaching agents |
| 0-10% | active substances or active ingredients for skin care products |
| 0-10% | further fillers |
| 0-10% | adjuvants |
| up to 100% | completed with water. |

A typical liquid W/O-make-up composition according to the invention, which, however, does not limit the invention, comprises the following components in wt.-%:

| | |
|---|---|
| 0.2-10% | polysiloxane compounds according to the invention |
| 0-5% | Co-emulsifiers |
| 10-50% | oil or combination of oils |
| 0-10% | stabilisers |
| 0-10% | consistency agents |
| 0-20% | UV filters |
| 2-20% | colorants and dye pigments |
| 0-10% | active substances or active ingredients for skin care products |
| 0-10% | further fillers |
| 0-10% | adjuvants |
| up to 100% | completed with water. |

A specific liquid W/O-skin make-up composition, which, however, does not limit the invention, comprises the following components in wt.-%:

| | |
|---|---|
| 0.5-6% | polysiloxane compounds according to the invention |
| 0-3% | Co-emulsifiers |
| 10-40% | oil or combination of oils |
| 0-5% | stabilisers |
| 0-5% | consistency agents |
| 4-15% | colorants and dye pigments |
| 0-20% | UV filters |
| 0-10% | active substances or active ingredients for skin care products |
| 0-10% | further fillers |
| 0-10% | adjuvants |
| up to 100% | completed with water. |

A typical W/O-mascara composition according to the invention, which, however, does not limit the invention, comprises the following components in wt.-%:

| | |
|---|---|
| 0.2-10% | polysiloxane compounds according to the invention |
| 0-5% | Co-emulsifiers |
| 10-50% | oil or combination of oils |
| 0-20% | stabilisers |
| 0-20% | consistency agents |
| 2-20% | colorants and dye pigments |

-continued

| | |
|---|---|
| 0-10% | further fillers |
| 0-10% | adjuvants |
| up to 100% | completed with water. |

A specific W/O-mascara composition, which, however, does not limit the invention, comprises the following components in wt.-%:

| | |
|---|---|
| 0.5-6% | polysiloxane compounds according to the invention |
| 0-3% | Co-emulsifiers |
| 10-40% | oil or combination of oils |
| 2-20% | stabilisers |
| 2-20% | consistency agents |
| 4-15% | colorants and dye pigments |
| 0-10% | active substances or active ingredients for skin care products |
| 0-10% | further fillers |
| 0-10% | adjuvants |
| up to 100% | completed with water. |

A typical W/O-anti-perspirant composition according to the invention, which, however, does not limit the invention, comprises the following components in wt.-%:

| | |
|---|---|
| 0.2-10% | polysiloxane compounds according to the invention |
| 0-5% | Co-emulsifiers |
| 10-50% | oil or combination of oils |
| 0-20% | stabilisers |
| 0-20% | consistency agents |
| 2-60% | anti-perspirant (active substance) |
| 0-10% | adjuvants |
| up to 100% | completed with water. |

A specific W/O-anti-perspirant composition, which, however, does not limit the invention, comprises the following components in wt.-%:

| | |
|---|---|
| 0.5-6% | polysiloxane compounds according to the invention |
| 0-3% | Co-emulsifiers |
| 10-40% | oil or combination of oils |
| 2-20% | stabilisers |
| 2-20% | consistency agents |
| 5-50% | anti-perspirant (active substance) |
| 0-10% | active substances or active ingredients for skin care products |
| 0-10% | adjuvants |
| up to 100% | completed with water. |

A typical W/O-hair treatment agent composition according to the invention, which, however, does not limit the invention, for conditioning (softening and improving the wet and dry combing potential), for hair-styling, for smoothing, curling, bleaching or colouring the hair comprises the following components in wt.-%:

| | |
|---|---|
| 0.2-10% | polysiloxane compounds according to the invention |
| 0-5% | Co-emulsifiers |
| 10-50% | oil or combination of oils |
| 0-20% | stabilisers |
| 0-20% | consistency agents |
| 0.1-20% | ingredient for hair products |
| 0-10% | adjuvants |
| up to 100% | completed with water. |

EXAMPLES

The following examples are supposed to explain the invention in more detail, without, however, limiting it.

Example 1

Production of a Copolymer Comprising Lactic Acid Ester-, Lauric Acid Ester- and Stearic Acid Ester Units.

1.33 g (14.76 mmol) DL-lactic acid, 5.49 g (27.41 mmol) lauric acid, 3.00 g (10.3 mmol) stearic acid, 0.4 g triethyl amine and 20.18 g (52.5 mmol epoxy groups) of a siloxane of the structure

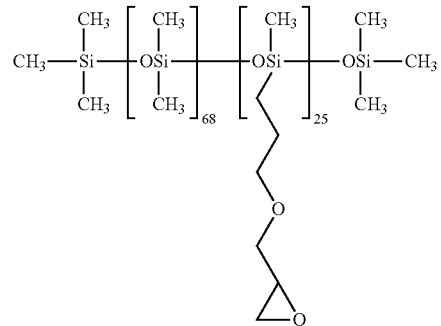

are dissolved in 70 g 1-methoxypropylacetate and heated for 12 hours to 120° C. After completion of the reaction all the volatile components in the vacuum are removed at 71° C./20 mbar within 2 hours. The solids content is 96.4% (15 min/160° C.).

A brown, clear polymer of the structure

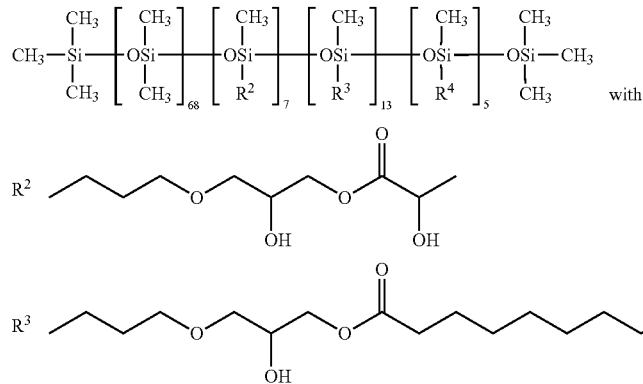

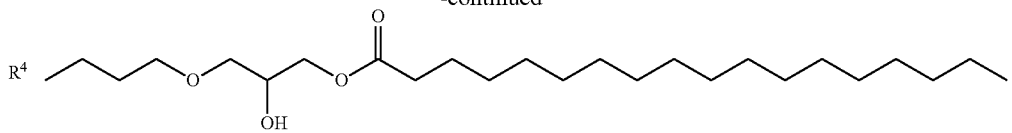

is obtained.

The molar ratio of the hydrophilic residues according to $R^{91}$ based on lactic acid ester units to the lipophilic residues according to $R^{92}$ based on lauric acid ester and stearic acid ester units is here approx. 7:(13+5)=approx. 1:2.6.

The molar ratio of the hydrophilic or lipophilic modified siloxy units, which comprise residues $R^{91}$ as well as $R^{92}$, to the non-modified siloxy units, which only comprise residues $R^8$, is here about 25/70=about 1:2.8.

Example 2

Production of a Copolymer Comprising Glycolic Acid Ester- and Stearic Acid Ester Units 0.98 g (12.87 mmol) glycolic acid, 11.57 g (40.66 mmol) stearic acid, 0.5 g triethyl amine and 17.45 g (53.5 mmol epoxy groups) of a siloxane of the structure

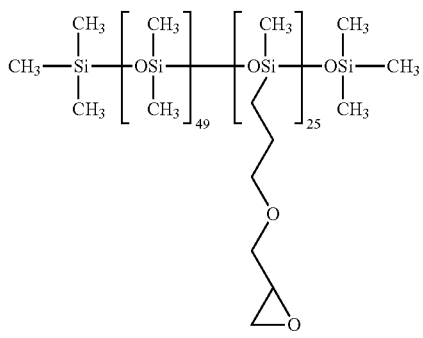

are dissolved in 70 g 1-methoxy-2-propanol and heated for 12 hours at 120° C.

After completion of the reaction all volatile components in the vacuum are removed at 71° C./20 mbar within 5 hours. The solids content represents 93.8% (15 min/160° C.).

A light brown, wax-like polymer of the structure

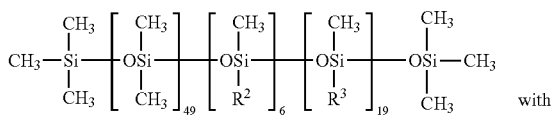

with

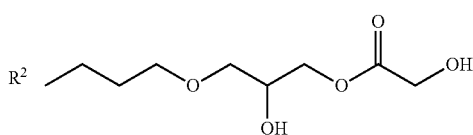

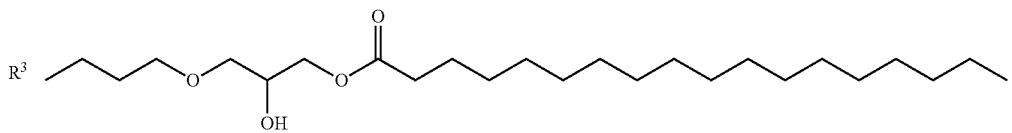

is obtained. The molar ratio of the hydrophilic residues according to $R^{91}$ based on glycolic acid ester units to the lipophilic residues according to $R^{92}$ based on stearic acid ester units is here approx. 6:19=approx. 1:3.2.

The molar ratio of the hydrophilic or lipophilic modified siloxy units to the non-modified siloxy units is here about 25/51=about 1:2.0.

Example 3

Production of a Copolymer Comprising Succinic Acid Glycerol Ester- and Stearic Acid Ester Units 11.3 g (122 mmol) glycerol, 12.3 g (122 mmol) succinic acid anhydride and 0.24 g triethyl amine are dissolved in 23.6 g 1-methoxypropyl acetate and heated at room temperature for 3 hours to 90° C. The complete opening of the anhydride ring under semi-ester formation was established by NMR spectroscopy.

4.72 g (12.3 mmol acid groups) of the solution of the succinic acid semi-ester, 16.56 g (51.2 mmol epoxy groups) of a siloxane of the structure

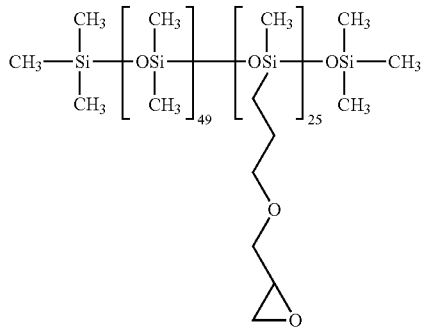

11.08 g (38.9 mmol) stearic acid and 0.54 g triethyl amine are dissolved in 67.64 g methoxypropyl acetate and heated for 12 hours to 120° C.

After completion of the reaction all volatile components in the vacuum are removed at 71° C./20 mbar within 5 hours. The solids content represents 86.7% (15 min/160° C.).

A light brown, wax-like polymer of the structure

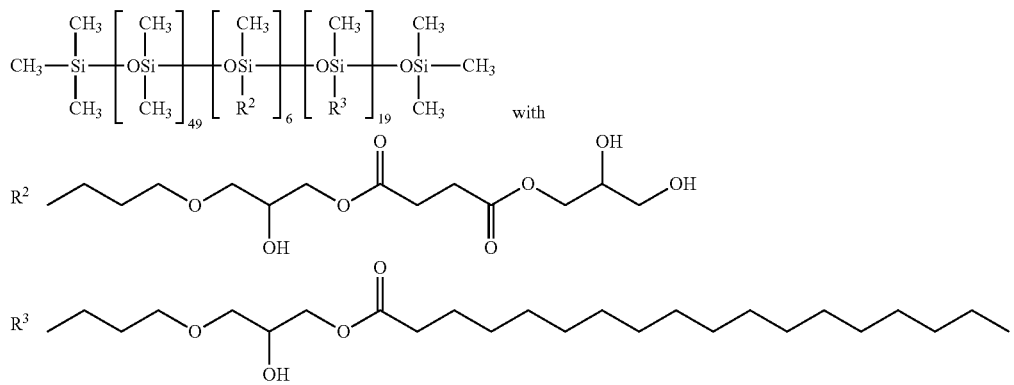

is obtained. The molar ratio of the hydrophilic residues corresponding to $R^{91}$ based on succinic acid ester units to the lipophilic residues $R^{92}$ based on stearic ester units here is approx. 6:19=approx. 1:3.2. The molar ratio of the hydrophilic or lipophilic modified siloxy units to the non-modified siloxy units here is about 25/51=about 1:2.0.

Example 4

Production of a Copolymer Comprising Lactic Acid Ester-, Lauric Acid Ester-, Stearic Acid Ester Units and N-Methyl Glucamine Units 0.6 g (7 mmol) DL-lactic acid, 3.0 g (15 mmol) lauric acid, 0.85 g (3 mmol) stearic acid, 0.1 g triethyl amine and 8.23 g (25 mmol epoxy groups) of a siloxane of the structure

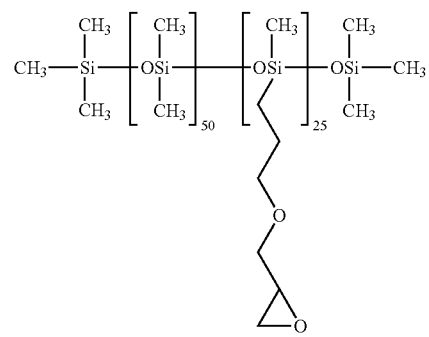

are dissolved in 29.8 g propylene glycol monomethylether and heated for 26 hours to 120° C.

At this point in time a conversion of epoxide groups of 95.8% was found.

Subsequently, 0.49 g (2.5 mmol) N-methylglucamine is added and the reaction is continued for 10 hours at 120° C.

An epoxide conversion of 100% is found.

After completion of the reaction the volatile components in the vacuum are removed at 70° C./20 mbar within 2 hours.

A brown, clear polymer of the approximate structure

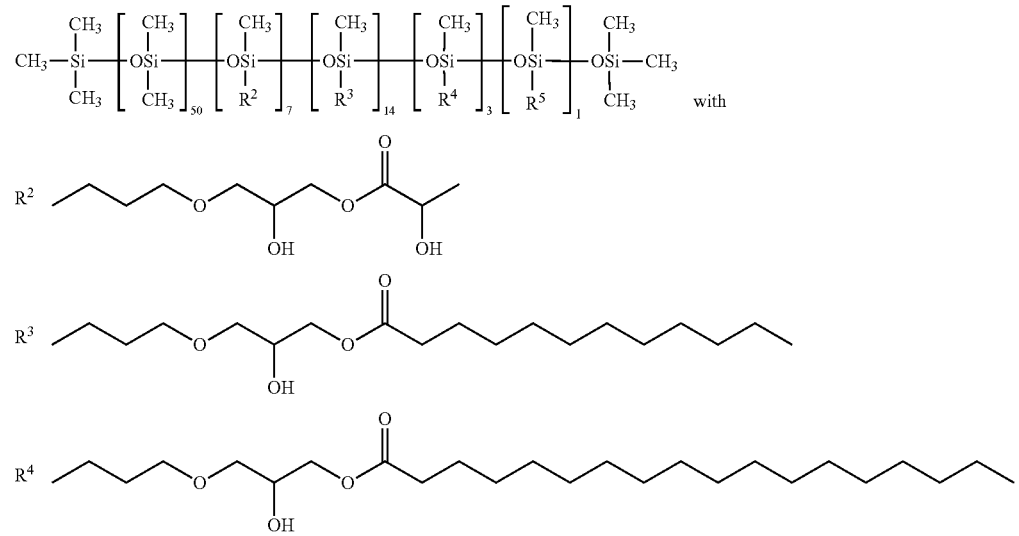

-continued

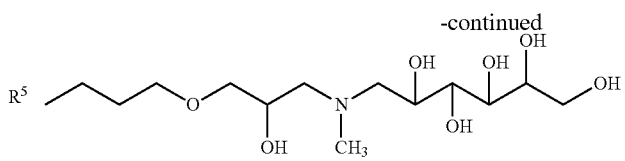

is obtained. The molar ratio of the hydrophilic residues corresponding to $R^{91}$ based on lactic acid ester- and N-methyl glucamine units to the lipophilic residues $R^{92}$ based on lauric acid ester- and N-methyl glucamine units here is approx. 8:17=approx. 1:2.1. The molar ratio of hydrophilic respectively lipophilic modified siloxy units to the non-modified siloxy units here is about 25/52=about 1:2.1.

Example 5

Production of W/O-Emulsions

W/O-emulsions of the following compositions are produced, wherein in each case a solution of glycerine and NaCl in water was slowly added to a pre-mixture of oil and the W/O-emulsifier according to the invention.

| | W/O Emulsion Example-No. | | | |
|---|---|---|---|---|
| | 5.1 | 5.2 | 5.3 | 5.4 |
| Mineral oil (g) | 2.5 | | | |
| D5 (g) | | 2.5 | | |
| Isopropyl myristate (g) | | | 2.5 | |
| Castor oil (g) | | | | 2.5 |
| Emulsifier Ex. 1 (g) | 0.11 | 0.11 | 0.11 | 0.11 |
| Water (g) | 7.1 | 7.1 | 7.1 | 7.1 |
| Glycerine (g) | 0.2 | 0.2 | 0.2 | 0.2 |
| NaCl (g) | 0.1 | 0.1 | 0.1 | 0.1 |
| Appearance W/O emulsion | creamy, highly viscous, light oil deposit | creamy, highly viscous | creamy, low viscosity | highly viscous, light water deposit |

| W/O Emulsion | 5.5 | 5.6 | 5.7 | 5.8 |
|---|---|---|---|---|
| Mineral oil (g) | 2.5 | | | |
| D5 (g) | | 2.5 | | |
| Isopropyl myristate (g) | | | 2.5 | |
| Castor oil (g) | | | | 2.5 |
| Emulsifier Ex. 2 (g) | 0.11 | 0.11 | 0.11 | 0.11 |
| Water (g) | 7.1 | 7.1 | 7.1 | 7.1 |
| Glycerine (g) | 0.2 | 0.2 | 0.2 | 0.2 |
| NaCl (g) | 0.1 | 0.1 | 0.1 | 0.1 |
| Appearance w/o emulsion | creamy, highly viscous | highly viscous | creamy, low viscosity | highly viscous, light water deposit |

D5 = decamethylcyclopentasiloxane

| W/O Emulsion | 5.9 | 5.10 | 5.11 | 5.12 |
|---|---|---|---|---|
| Mineral oil (g) | 2.5 | | | |
| D5 (g) | | 2.5 | | |
| Isopropyl myristate (g) | | | 2.5 | |
| Castor oil (g) | | | | 2.5 |
| Emulsifier Ex. 3 (g) | 0.11 | 0.11 | 0.11 | 0.11 |
| Water (g) | 7.1 | 7.1 | 7.1 | 7.1 |
| Glycerine (g) | 0.2 | 0.2 | 0.2 | 0.2 |
| NaCl (g) | 0.1 | 0.1 | 0.1 | 0.1 |

| W/O Emulsion | 5.9 | 5.10 | 5.11 | 5.12 |
|---|---|---|---|---|
| Appearance w/o emulsion | creamy, highly viscous | creamy, very highly viscous | creamy, low viscosity, light oil deposit | highly viscous, light water deposit |

| W/O Emulsion | 5.13 | 5.14 | 5.15 | 5.16 |
|---|---|---|---|---|
| Mineral oil (g) | 2.5 | | | |
| D5 (g) | | 2.5 | | |
| Isopropyl myristate (g) | | | 2.5 | |
| Castor oil (g) | | | | 2.5 |
| Emulsifier Ex. 4 (g) | 0.11 | 0.11 | 0.11 | 0.11 |
| Water (g) | 7.1 | 7.1 | 7.1 | 7.1 |
| Glycerine (g) | 0.2 | 0.2 | 0.2 | 0.2 |
| NaCl (g) | 0.1 | 0.1 | 0.1 | 0.1 |
| Appearance w/o emulsion | creamy, highly viscous | creamy, very highly viscous | creamy, low viscosity | highly viscous, light water deposit |

The data on the formulations 5.1 to 5.16 indicate that the emulsifiers according to the invention comprise a broad spectrum with respect to the tolerable oil phase for the emulsification. Non-polar oils (mineral oils), semi-polar oils (isopropyl myristate, D5 (decamethylcyclopentasiloxane)) and strong polar oils (castor oil) can be used.

Example 6

Starting Material

Production of Stearic Acid Allyl Ester 569 g (2 mol) stearic acid are provided under $N_2$ and heated to 80° C.

262 g (2.2 mol) $SOCl_2$ are added dropwise and the mixture is heated for 2 hours to 95° C. Subsequently, all volatiles up to 95° C./20 mbar are distilled off.

Within 30 minutes 139.2 g (2.4 mol) allyl alcohol is added dropwise at 80° C. and the mixture is stirred for a further 1 hour at this temperature.

The raw product is washed with 500 ml of a 20-% $NaHCO_3$ solution followed by 3 times 500 ml deionised water and then air-dried.

Yield 584 g of stearic acid allyl:

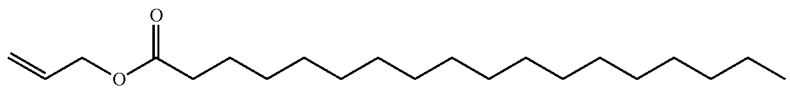 [SMILES: C=CCOC(=O)CCCCCCCCCCCCCCCCC]

Using this starting material a lipophilic residue corresponding to $R^{92}$ can be introduced into SiH-functional starting polysiloxanes via hydro silylation.

Example 7

Starting Material

Production of an Ester from Lauric Acid and Propoxylated Allyl Alcohol.

600 g (3 mol) lauric acid are provided under $N_2$ and heated to 60° C.

392.7 g (3.3 mol) $SOCl_2$ are added dropwise within 30 minutes and the mixture is heated for 2 hours to 70° C. Subsequently, all volatiles up to 70° C./20 mbar are distilled off.

650 g lauric acid chloride are obtained.

In a separate flask 471 g (3.12 mol) of a propoxylated allyl alcohol of the structure

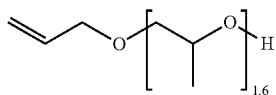

is provided under $N_2$ and heated to 80° C. Within 1 hour 650 g lauric acid chloride is added dropwise and the mixture stirred for a further 2 hours. All components simmering up to 150° C./20 mbar are distilled off.

Yield 934 g of an ester of the structure:

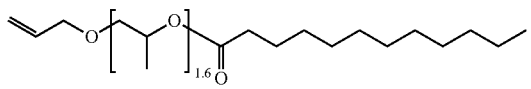

Using this starting material a lipophilic residue corresponding to $R^{92}$ can be introduced into SiH-functional starting polysiloxanes via hydrosilylation.

Example 8

Production of a Copolymer Comprising Oleic Acid Ester and N-Methyl Glucamine Units 14.12 g (50 mmol) oleic acid, 0.5 g triethyl amine and 31.58 g (50 mmol epoxy groups) of a siloxane of the structure

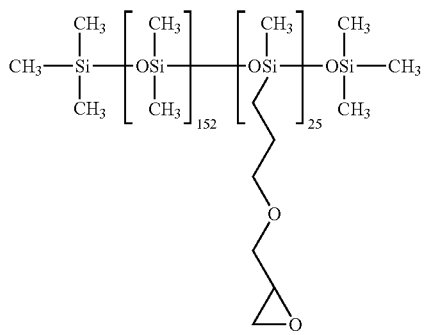

are dissolved in 70 g 1-methoxy-2-propanol and heated for 12 hours to 120° C.

Conversion is 90.9% determined by $^1$H-NMR.

Subsequently, 0.98 g (5 mmol) N-methylglucamine is added and the reaction is continued for 8 hours at 120° C. After completion of the reaction the volatile components in the vacuum are removed at 70° C./20 mbar within 2 hours.

Conversion is 100% determined by $^1$H-NMR.

A light brown, oily polymer of the approximate structure

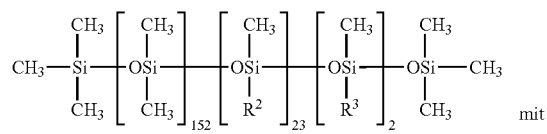

mit

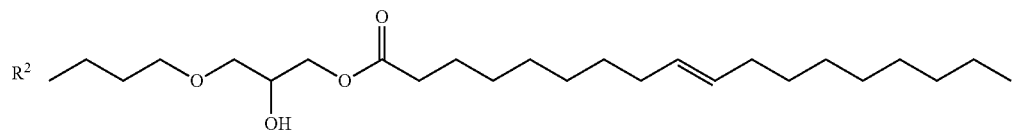

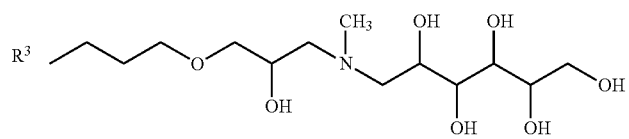

is obtained, wherein $R^{91}$:$R^{92}$ is 2:23.

Example 9

Production of W/O-Emulsions

W/O-emulsions of the following compositions are produced, wherein in each case a titration solution (II) consisting of water, glycerine and NaCl was slowly added to a pre-mixture (I) of oil and the W/O-emulsifier, i.e. the polysiloxane according to the invention. This titration solution was prepared by mixing 355 g water with 10 g glycerine and 5 g NaCl.

| W/O Emulsion | 9.1 | 9.2 | 9.3 | 9.4 | 9.5 |
|---|---|---|---|---|---|
| D5 (g) | 25 | | | 25 | |
| Mineral oil (g) | | 25 | | | |
| Isopropyl myristate (g) | | | 25 | | 25 |
| Emulsifier of Example 8 (g) | 1.1 | 1.1 | 1.1 | 1.1 | 1.1 |
| Titration solution (g) | 70 | 70 | 70 | 120 | 120 |
| Stability Emulsion 14 days RT* | 4 | 5 | 5 | 5 | 5 |
| Viscosity Emulsion 14 days RT** | 4 | 5 | 2 | 5 | 5 |
| Skin feel*** | | 4 | | 5 | 5 |
| Spreadability**** | | 5 | | 5 | 5 |

Stability Emulsion 14 days RT (room temperature)*: Scale 1 to 5 with 1 = complete separation into oil and water and 5 = completely homogenous.
Viscosity Emulsion 14 days RT**: Scale 1 to 5 with 1 = low viscosity close to water and 5 = stable at shaking
Skin feel***: Scale 1 to 5 with 1 = strongly adhesive to 5 = soft, waxy
Spreadability****: Scale 1 to 5 with 1 = rubber-like, high resistance to 5 = easily spreadable without resistance.

The data indicate that by using the emulsifiers according to the invention large amounts of water can be taken up by the emulsion formulations. Specifically an increase in water content leads to an increase in viscosity and thus stability of the formulation is improved. This applies for siloxan-based systems like D5 as well as oil-based system like isopropyl myristate. Skin feel and Spreadability are very good.

Example 10

Production of a Copolymer Comprising Stearic Acid Ester and N-Methyl Glucamine Units 85.07 g (300 mmol) stearic acid, 1.25 g triethyl amine and 164.9 g (300 mmol epoxy groups) of a siloxane of the structure

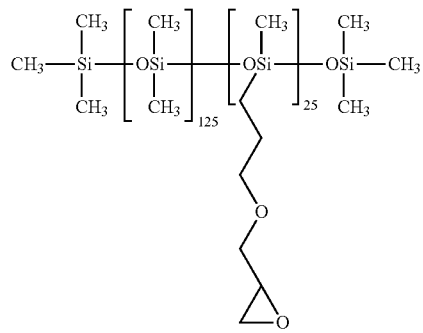

are dissolved in 107 g propylene glycol monomethylether and heated for 10 hours to 120° C. Using these reaction conditions a conversion of 97.1% of the epoxy groups is found by control of $^1$H-NMR. Subsequently, 5.84 g (30 mmol) N-methylglucamine is added and the reaction is continued for 4 hours at 120° C. Epoxy group conversion is 100%. After completion of the reaction the volatile components are removed in the vacuum at 70° C./20 mbar within 2 hours.

A yellow grey waxy polymer of the average structure

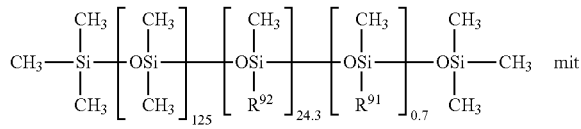
mit

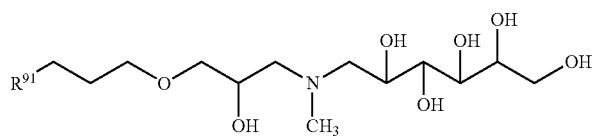

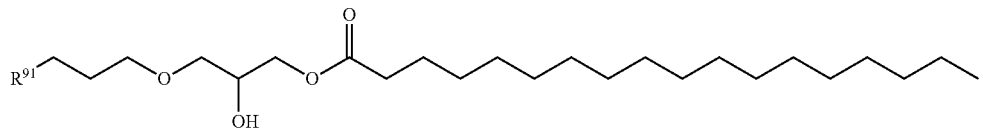

is obtained, wherein $R^{91}:R^{92}$ is 0.7:24.3.

Example 11

Production of a Copolymer Comprising Stearic Acid Ester, Oleic Acid Ester and Diethyl Amine Units 21.62 g (76 mmol) stearic acid, 6.78 g (24 mmol) oleic acid 0.5 g triethyl amine and 53.67 g (100 mmol epoxy groups) of a siloxane of the structure

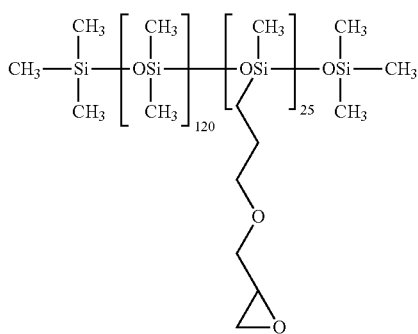

are dissolved in 35 g propylene glycol monomethylether and heated for 10 hours to 120° C. Subsequently, 0.73 g (10 mmol) diethyl amine is added and the reaction is continued for 4 hours at 120° C. Epoxy group conversion is 100%.

After completion of the reaction the volatile components in the vacuum are removed at 70° C./20 mbar within 2 hours.

A yellow waxy polymer of the average structure

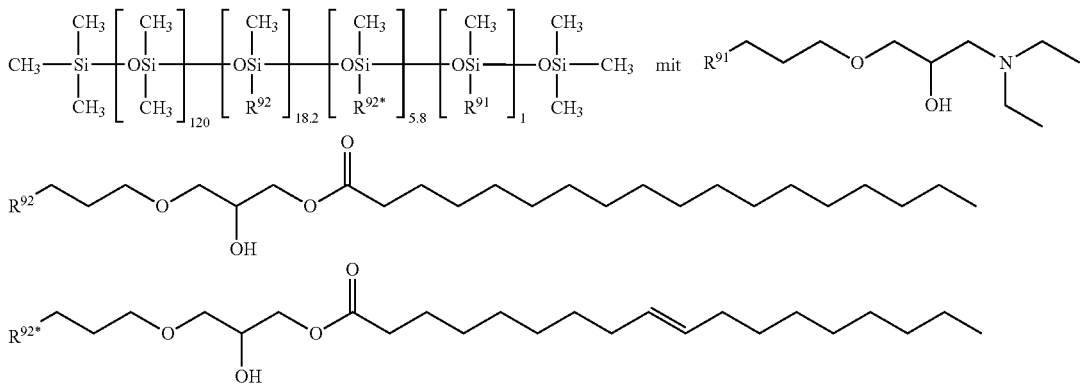

is obtained, wherein $R^{91}$:$R^{92}$ is 1:24.

Example 12

Production of a Copolymer Comprising Two Different Ester Units, i.e. Stearic Acid Ester and Lactic Acid Units and N-Methyl Glutamine Units a) 22 g (68.9 mmol) Oleic acid propargyl ester and 10.5 g (91.8 mmol) allylglycidylether are heated in $N_2$ atmosphere to 80° C. 2 g (9.18 mmol SiH) of an SiH oil of the structure M-$D_{55}$-$D^H{}_{25}$-M and subsequently 0.1 g of a 1% Pt containing solution of $H_2PtCl_6$ in ethanol were added dropwise. Temperature rose to 140° C. and within 0.5 hours additional 23 g (105.6 mmol SiH) of the SiH oil of the structure M -$D_{55}$-$D^H{}_{25}$-M were added dropwise. Reaction is continued for 2 hours at 140° C. Subsequently the components volatile up to 150° C./20 mbar are removed. A yellowish turbid viscous oil is obtained.

b) 2.82 g (10 mmol) oleic acid, 0.9 g (10 mmol) lactic acid, 0.46 g triethyl amine and 23.37 g (2 mmol) of the epoxy and oleic acid ester units comprising siloxan according to step a) are dissolved in 63 g propylene glycol monomethylether and heated for 10 hours to 120° C. Subsequently, 0.98 g (5 mmol) N-methylglucamine is added and the reaction is continued for 4 hours at 120° C. Epoxy group conversion is 100%.

After completion of the reaction the volatile components are removed in the vacuum at 70° C./20 mbar within 2 hours.

A brown waxy polymer is obtained, which shows $^1$H-NMR signals of propenylester groups attached to the silicon atoms, reaction products of propyloxy epoxy groups attached to the silicon atoms with lactic acid, oleic acid and with N-methyl-glucamine.

Example 13

Production of a Copolymer Comprising Two Different Units, i.e. Oleic Ester and N-Methyl Glucamine Units a) 15 g (47 mmol) oleic acid propargyl ester and 3.5 g (31 mmol) propargyl glycidyl ether are dissolved under $N_2$ in 70 ml toluene and subsequently 0.1 g of a 1% Pt containing solution of $H_2PtCl_6$ in ethanol is added dropwise. The mixture is heated to 140° C. Within 0.5 hours a mixture, consisting of 17.23 g (75 mmol SiH) of an SiH oil of the structure M-$D_{55}$-$D^H{}_{25}$-M and 30 g toluene is added dropwise and the temperature is maintained for 4 hours.

Subsequently the components volatile up to 150° C./20 mbar are removed. A yelloxy brown liquid is obtained.

b) 1.41 g (5 mmol) oleic acid, 0.2 g triethyl amine and 7 g (0.566 mmol) of the epoxy and oleic acid ester units comprising siloxan according to step a) are dissolved in 30 g propylene glycol monomethylether and heated for 10 hours to 120° C. Subsequently, 0.14 g (0.7 mmol) N-methylglucamine is added and the reaction is continued for 4 hours at 120° C. Epoxy group conversion is 100%.

After completion of the reaction the volatile components are removed in the vacuum at 70° C./20 mbar within 2 hours. A dark brown pasty polymer is obtained, which shows $^1$H-NMR signals of propenylester groups attached to the silicon atoms, reaction products of the epoxy group attached by propenyloxy groups to the silicon atoms with N-methylglucamine.

Example 14

Production of a Copolymer Comprising Oleic Acid Ester, Lactic Acid and N-Methyl Glucamine Units 0.45 g (5 mmol) lactic acid, 0.2 g triethyl amine and 7 g (0.566 mmol) of the epoxy and oleic acid ester units comprising Siloxans obtained according to example 13 a) are dissolved in 30 g propylene glycol monomethylether and heated for 10 hours at 120° C. Subsequently, 0.98 g (5 mmol) N-methylglucamine is added and the reaction is continued for 4 hours at 120° C. Epoxy group conversion is 100%.

After completion of the reaction the volatile components are removed in the vacuum at 70° C./20 mbar within 2 hours. A brown pasty polymer is obtained, which shows $^1$H-NMR signals of propenylester groups attached to the silicon atoms, reaction products of the epoxy group attached by a propenyloxy group to the silicon atoms with lactic acid and with N-methylglucamine.

Example 15

Production of a Copolymer Comprising Octadecyl, Oleic Ester, Lactic Acid Ester and N-Methyl Glucamine Units a) 22.7 g (90 mmol) octadecene and 8.9 g (78 mmol) allyl glycidyl ether are dissolved under $N_2$ in 60 g 2-propanol. The mixture is heated under reflux and 6.3 g (16.8 mmol) of an SiH oil of the structure M-$D_{90}$-$D^H_{25}$-M and subsequently 0.2 g of a 1% Pt containing solution of $H_2PtCl_6$ in ethanol were added dropwise. Within 0.25 hours additional 50 g (133.2 mmol SiH) of the SiH oil of the structure M-$D_{90}$-$D^H_{25}$-M were added dropwise and the temperature is maintained for 4 hours. Subsequently the components volatile up to 150° C./20 mbar are removed. A brown goopy waxy polymer is obtained.

b) 2.85 g (10 mmol) stearic acid, 0.9 g (10 mmol) lactic acid and 0.5 g triethyl amine and 26.54 g (2 mmol) of the octadecyl units and epoxy units containing siloxan obtained in step a) were dissolved in 71 g propylene glycol monomethylether and heated for 10 hours to 120° C.

Subsequently, 0.39 g (2 mmol) N-methylglucamine is added and the reaction is continued for 4 hours at 120° C. Epoxy group conversion is 100%. The product shows $^1$H-NMR signals of C18-alkyl groups attached to the silicon atoms, reaction products of the epoxy group attached by a propyloxy group to the silicon atoms with lactic acid, stearic acid and with N-methylglucamine.

Example 16

Production of W/O-Emulsions

W/O-emulsions of the following compositions are produced, wherein in each case a mixture (II) consisting of 100 g water, 1.4 g NaCl and 2.8 g glycerine, was added to a pre-mixture (I) of oil and the W/O-emulsifier, the polysiloxane according to the invention with stirring.

| | W/O Emulsion Example-No. | | | |
|---|---|---|---|---|
| | 16.1 | 16.2 | 16.3 | 16.4 |
| D5 (g) | 25 | | 25 | |
| Mineral oil (g) | | 25 | | 25 |
| Mixture (g) Water/NaCl/Glycerine | 102 | 84 | 124 | 102 |
| Emulsifier Ex. 10 (g) | 1.1 | 1.1 | | |
| Emulsifier Ex. 11 (g) | | | 1.1 | 1.1 |
| Appearance W/O emulsion | creamy, highly viscous | creamy, highly viscous | creamy, highly viscous | creamy, highly viscous |

| | W/O Emulsion Example-No. | | | | | |
|---|---|---|---|---|---|---|
| | 16.5 | 16.6 | 16.7 | 16.8 | 16.9 | 16.10 |
| D5 (g) | 25 | | 25 | | 25 | |
| Mineral oil (g) | | 25 | | 25 | | 25 |
| Mixture (g) Water/NaCl/Glycerine | 94 | 103 | 70 | 70 | 70 | 87 |
| Emulsifier Ex. 12 (g) | 1.1 | 1.1 | | | | |
| Emulsifier Ex. 13 (g) | | | 1.1 | 1.1 | | |
| Emulsifier Ex. 14 (g) | | | | | 1.1 | 1.1 |
| Appearance W/O emulsion | creamy, highly viscous | creamy, highly viscous | creamy, low viscosity | creamy, low viscosity | creamy, low viscosity | creamy, highly viscous |

The invention claimed is:

1. Polysiloxane compounds of the formula:

$$[M_a D_b T_c Q_d]_e \quad (I)$$

wherein
$M = R_3SiO_{1/2}$,
$D = R_2SiO_{2/2}$,
$T = RSiO_{3/2}$,
$Q = SiO_{4/2}$,
with
a = 1-10
b = 0-1000
c = 0-1
d = 0-1
e = 1-10
wherein
R = is an organic group,
with the requirement that R comprises hydrophilic residues $R^{91}$ and lipophilic residues $R^{92}$
wherein
$R^{91}$ is selected from the group consisting of:
  $R^{11}$—Z-(A-$E^1$)$_y$, wherein
  Z = a bivalent or trivalent straight-chained, cyclic or branched, saturated or unsaturated $C_2$ to $C_{20}$-hydrocarbon residue, which can comprise one or more groups selected from —O—, —NH—,

and can be substituted by one or more OH groups,
A is a bivalent residue which is selected from the group consisting of:

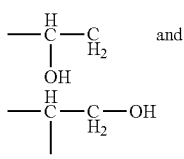 and

wherein y=1 or 2,
E$^1$ is selected from the group consisting of:
E$^{22}$=—O—C(O)—R$^{22}$,
  wherein R$^{22}$=a straight-chained, cyclic or branched, saturated or unsaturated hydrocarbon residue with up to 9 carbon atoms, which can comprise one or more groups selected from —O—, —NH—, —NR$^3$—, —C(O)—, and is substituted by one or more OH groups, wherein R$^3$=a straight-chained, cyclic or branched, saturated or unsaturated hydrocarbon residue with up to 6 carbon atoms,
E$^{31}$=

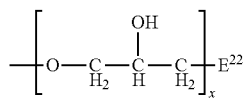

wherein x=1-4, and
E$^{51}$=—NR$^{41}$R$^{51}$, wherein
  R$^{41}$ and R$^{51}$ are the same or different and selected from the group consisting of hydrogen and a straight-chained, cyclic or branched, saturated or unsaturated hydrocarbon residue with up to 9 carbon atoms, which can comprise one or more groups selected from —O—, —NH—, —NR$^3$—, wherein R$^3$, as defined above, can comprise —C(O)— and can be substituted by one or more OH and/or H$_2$N groups,
R$^{61}$=—Z-E$^{22}$, and
R$^{71}$=—Z-E$^{61}$, wherein E$^{61}$=—NH—C(O)—R$^{41}$, and
R$^{92}$ is selected from the group consisting of:
R$^{12}$=—Z-(A-E$^2$)$_y$, wherein
E$^2$ is selected from the group consisting of:
E$^{23}$=—O—C(O)—R$^{23}$,
  wherein R$^{23}$=a straight-chained, cyclic or branched, saturated or unsaturated hydrocarbon residue with 10 to 50 carbon atoms, which can comprise one or more groups selected from —O—, —NH—, —NR$^3$—, —C(O)—, and can be substituted by one or more OH groups, wherein R$^3$=a straight-chained, cyclic or branched, saturated or unsaturated hydrocarbon residue with up to 6 carbon atoms,
E$^{32}$=

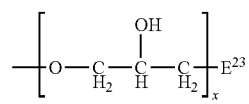

and x=1-4, and
E$^{52}$=—NR$^{42}$R$^{52}$, wherein
  R$^{42}$ and R$^{52}$ are the same or different and are selected from the group consisting of a hydrogen and straight-chained, cyclic or branched, saturated or unsaturated hydrocarbon residue with 10 to 30 carbon atoms, which can comprise one or more groups selected from —O—, —NH—, —NR$^3$—, —C(O)—, and can be substituted by one or more OH— and/or H$_2$N groups, and
R$^{62}$=—Z-E$^{23}$, and
R$^{72}$=—Z-E$^{62}$, wherein E$^{62}$=—NH—C(O)—R$^{42}$.

2. Polysiloxane compounds according to claim 1, wherein the hydrophilic residues R$^{91}$ have a logP (25° C.) of <0.5 and
the lipophilic residues R$^{92}$ have a logP (25° C.) of ≥0.5, determined on the basis of the corresponding compounds H—R$^{91}$ and H—R$^{92-}$.

3. Polysiloxane compounds according to claim 1, wherein R=methyl,
Z=is selected from the group consisting of —CH$_2$CH$_2$CH$_2$—O—CH$_2$—, —CH$_2$CH$_2$CH$_2$—,

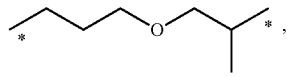

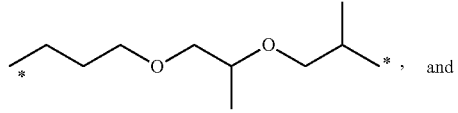 and

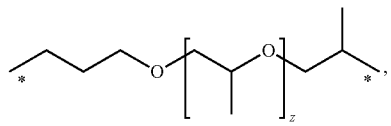

wherein z=1 to 4,
wherein * denotes a bond,
—CH=CH$_2$CH$_2$—, —CH=CH$_2$CH$_2$CH$_2$—,

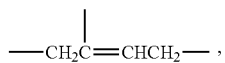

wherein the bond to the silicon takes place at the 2-position, and
x=1.

4. The process for the production of the polysiloxane compounds according to claim 1, wherein
(a) an epoxy-functional polysiloxane is reacted with one or more carboxylic acids and subsequently with primary or secondary amines, if necessary,
(b) an epoxy-functional polysiloxane is reacted with one or more carboxylic acids and carboxylic acid anhydrides, wherein carboxylic acid anhydrides are partially esterified by adding mono or multivalent alcohols, and subsequently also reacted with primary or secondary amines,
(c) a SiH-functional polysiloxane is reacted with
  (i) one or more mono-functional olefinically or acetylenically unsaturated ethers of glycerine or of glycerine oligomers, at least one hydroxyl group of which is esterified, and
  (ii) one or more esters of fatty acids with unsaturated alcohols, or
(d) amino-functional polysiloxanes are reacted with carboxylic acids or with epoxy-functional compounds.

5. The process according to claim 4, wherein the unsaturated alcohols are selected from the group consisting of monols; diols; alkenols; alkynols; CH$_2$=CHCH$_2$OH;

CH$_2$=CHCH$_2$CH$_2$OH; CH$_2$=CHCH$_2$CH$_2$CH$_2$CH$_2$OH; CH≡CCH$_2$OH; HOCH$_2$C≡CCH$_2$OH; HOCH$_2$CH=CHCH$_2$OH; CH≡CHCH$_2$CH$_2$CH$_2$CH$_2$OH; hexynediols; HOCH$_2$CH$_2$C≡CCH$_2$CH$_2$OH; ethylenoxide-free poly(alkoxylates) of alkenols or alkynols, and ethylenoxide-free (poly)propoxylates of alkenols or alkynols.

6. The process according to claim 4, wherein the fatty acids are monocarboxylic acids which lack hydrosilylated groups selected from the group consisting of acetic acid, caprionic acid, 2-ethyl caprionic acid, lauric acid, tetradecenoic acid, capriodecenoic acid, octadecenoic acid, oleic acid, linoleic aci,d linolenic acid and elaidic acid.

7. An emulsifier comprising the polysiloxane polymers according to claim 1.

8. A cosmetic formulation comprising the polysiloxane polymers according to claim 1.

9. A sun screen formulation comprising the cosmetic formulation of claim 8.

10. A defoaming composition comprising the polysiloxane polymers according to claim 1.

11. A foam stabilizer for polyurethane foams comprising the polysiloxane polymers according to claim 1.

12. An agriculture composition comprising the polysiloxane polymers according to claim 1.

13. Water in oil emulsions comprising the polysiloxane polymers of claim 1.

* * * * *